US006233470B1

(12) United States Patent
Tsuchiya

(10) Patent No.: US 6,233,470 B1
(45) Date of Patent: May 15, 2001

(54) ABSORPTION INFORMATION MEASURING METHOD AND APPARATUS OF SCATTERING MEDIUM

(75) Inventor: Yutaka Tsuchiya, Hamamatsu (JP)

(73) Assignee: Hamamatsu Photonics K.K., Hamamatsu (JP)

(*) Notice: Subject to any disclaimer, the term of this patent is extended or adjusted under 35 U.S.C. 154(b) by 0 days.

(21) Appl. No.: 09/414,822

(22) Filed: Oct. 8, 1999

Related U.S. Application Data

(62) Division of application No. 08/919,207, filed on Aug. 28, 1997, now Pat. No. 5,983,121.

(30) Foreign Application Priority Data

Aug. 30, 1996 (JP) .................................................. 8-230683

(51) Int. Cl.[7] .................................................. A61B 5/00
(52) U.S. Cl. .................... 600/310; 600/322; 600/473; 600/476; 356/432
(58) Field of Search .................................... 600/310, 322, 600/323, 330, 473, 476; 356/432, 433; 250/339.12, 341.1

(56) References Cited

U.S. PATENT DOCUMENTS

| 4,972,331 | 11/1990 | Chance ................................ 600/310 |
| 5,187,672 | 2/1993 | Chance et al. ....................... 600/407 |
| 5,441,054 | 8/1995 | Tsuchiya . |
| 5,477,051 | 12/1995 | Tsuchiya .......................... 250/341.1 |
| 5,713,352 | 2/1998 | Essenpreis et al. ................. 600/473 |
| 5,770,454 | 6/1998 | Essenpreis et al. ................. 600/310 |

FOREIGN PATENT DOCUMENTS

| 0 703 445 | 3/1996 | (EP) . |
| 8-94517 | 4/1996 | (JP) . |
| 95/32416 | 11/1995 | (WO) . |

OTHER PUBLICATIONS

Tsuchiya et al., "Non–Invasive Spectroscopy of Variously Shaped Turbid Media Like Human Tissue Based on the Microscopic Beer–Lambert Law", OSA Tops on Biomedical Optical Spectroscopy and Diagnostics 1996, vol. 3, 1996 Optical Society of America, pp. 98–100.

Tsuchiya et al., "Non–Invasive Spectroscopy of Turbid Media Having Various Non–Reentrant Surfaces (1)", Japan Optics '95, pp. 61–62.

Tsuchiya et al., "Frequency Domain Analysis of Photon Migration Based on the Microscopic Beer–Lambert Law", Jpn. J. Appl. Phys., vol. 35, 1996, pp. 4848–4851.

*Primary Examiner*—Eric F. Winakur
(74) *Attorney, Agent, or Firm*—Pillsbury Winthrop LLP

(57) ABSTRACT

A method characterized by making modulated light having a predetermined modulation frequency component, incident to a scattering medium, receiving the modulated light having propagated inside the scattering medium to acquire measurement signals, detecting signals of the foregoing modulation frequency component from the measurement signals, obtaining amplitudes and inclinations of phase against modulation angular frequency, of the signals of the foregoing modulation frequency component, calculating a difference between absorption coefficients being primary information, based on a predetermined relation among the amplitudes, the inclinations of phase against modulation angular frequency and the difference between absorption coefficients, and calculating a difference of concentration of an absorptive constituent being secondary information, based on the difference between absorption coefficients.

10 Claims, 10 Drawing Sheets

TRACK OF PHOTON HAVING PROPAGATED
INSIDE SCATTERING MEDIUM

NEAR-INFRARED ABSORPTION SPECTRA
OF Hb(0.37mM), Mb(0.15mM).

ABSOLUTE SPECTRA
SOLID LINES:OXYGENATED
DOTTED LINES:DEOXYGENATED

ABSORPTION SPECTRA OF
VARIOUS LIVING SUBSTANCES

GENERATION OF MODULATED
LIGHT BY LASER DIODE

GENERATION OF MODULATED
LIGHT BY USE OF BEAT
(USING TWO CW LASERS)

GENERATION OF MODULATED
LIGHT BY OPTICAL MODULATOR

CONDENSER LENS

OPTICAL FIBER

PINHOLE

INCIDENCE OF LIGHT FROM INSIDE SCATTERING MEDIUM

DIRECT DETECTION

OPTICAL FIBER

COMBINATION WITH LENS

ABSORPTION INFORMATION MEASURING METHOD AND APPARATUS OF SCATTERING MEDIUM

This is a division of application Ser. No. 08/919,207, filed Aug. 28, 1997 now U.S. Pat. No. 5,983,121.

BACKGROUND OF THE INVENTION

1. Field of the Invention

The present invention relates to a method and an apparatus for measuring absorption information of a scattering medium and, more particularly, to a method and apparatus for measuring a temporal change or a spatial distribution of concentration of an absorptive constituent in a scattering medium having non-reentrant surfaces. The invention further concerns a method and apparatus for measuring a concentration of an absorptive constituent inside the scattering medium by use of light of plural wavelengths.

2. Related Background Art

There are very strong demands for non-invasive and precise measurements of absorption information including a concentration of a specific absorptive constituent inside a scattering medium like a living body, a temporal change or a spatial distribution thereof, and so on. Attempts of various methods have been made heretofore, including methods using continuous wave light (cw light) and modulated light (for example, pulsed light, square-wave light, sine-wave modulated light, etc.), methods utilizing light of different wavelengths (multi-wavelength spectroscopy), and so on.

These conventional technologies, however, are not yet capable of accurately measuring the concentration of the specific absorptive constituent inside for tissues and organs having various shapes like the living body or for objects having individual differences of shape though being tissues or organs of a same kind. This presents a serious problem for non-invasive measurements of living body utilizing light, and improvements therein are strongly desired.

Light incident to the scattering medium like the living body propagates inside, is scattered and absorbed therein, and then part of the light emerges from its surface. Since the outside of the scattering medium is normally air, the light emerging from the surface is dispersed in the free space. The light emerging from the surface as described above is detected in measurements of internal information of scattering medium. At this time the propagating light spreads throughout the entire region of scattering medium and is dispersed from the whole surface to the outside. Therefore, when the output light is detected at a specific position in the surface, the quantity or a time-resolved waveform of detected light greatly varies with change in the shape of medium, for example, depending upon whether it is a sphere or a rectangular parallelepiped.

In order to enhance the measurement accuracy in the cases as described above, it is necessary to sufficiently understand the behavior of light inside the scattering medium. Recently, the behavior of light inside the scattering medium has been analyzed, tested, or investigated by Monte Carlo simulations with a to computer. It is also known that the behavior can be described and analyzed accurately to some extent by the photon diffusion theory. The Monte Carlo simulations, however, require an extremely long calculation time and do not allow calculation of a concentration of a specific absorptive constituent inside the scattering medium from their results. In utilizing the photon diffusion theory, it is necessary to set boundary conditions for solving the photon diffusion equation. However, since the boundary conditions differ greatly depending upon the shape of scattering medium, new boundary conditions must be set to solve the photon diffusion equation for every change in the shape of scattering medium, in order to achieve accurate measurement. Scattering media for which the boundary conditions can be set accurately to some extent are limited to very simple shapes such as an infinite space, a semi-infinite space, an infinite cylinder, or a slab spreading infinitely and having a finite thickness. As a result, use of approximate boundary conditions is indispensable to measurements of living tissues having complicated shapes, which is a cause to produce large measuring errors.

The above problems are also discussed, for example, in the recent literature: Albert Cerussi et al., "The Frequency Domain Multi-Distance Method in the Presence of Curved Boundaries," in Biomedical Optical Spectroscopy and Diagnostics, 1996, Technical Digest (Optical Society of America, Washington D.C., 1996) pp. 24–26.

As described above, there are no methods for measuring absorption information sufficient to be systematically applied to scattering media of different shapes, and it was extremely difficult for conventional technologies to systematically accurately and efficiently measure the concentration of a specific absorptive constituent or the like in the scattering media of different shapes.

SUMMARY OF THE INVENTION

The present invention has been accomplished in view of the problems in the conventional technologies described, above. An object of the invention is to newly disclose a method for describing the behavior of light inside the scattering media of different shapes (basic relations) and to provide a measuring method and measuring apparatus for measuring absorption information inside the scattering medium, realizing measurements of change, absolute value, or the like of concentration of a specific absorptive constituent in the scattering media of various shapes by use of the relations. The measurement accuracy thereof is greatly improved and a temporal change or a spatial distribution can be efficently measured.

A first absorption information measuring method of scattering medium according to the present invention is a method comprising: (a) making modulated light having a predetermined modulation frequency component, incident in a spot shape to a surface of a scattering medium being a measured object; (b) receiving said modulated light having propagated inside the measured object at a plurality of timings and/or at a plurality of positions in the surface of said scattering medium to acquire measurement signals each thereat; (c) detecting signals of said modulation frequency component each from said measurement signals; (d) obtaining sine components and inclinations of cosine component against modulation angular frequency, of the signals of said modulation frequency component obtained in respective measurements at said plurality of timings and/or at said plurality of positions; and (e) based on a predetermined relation among said sine components, said inclinations of cosine component against modulation angular frequency, and a difference between absorption coefficients at said plurality of timings and/or at said plurality of positions, calculating said difference between absorption coefficients being primary information.

Also, a second absorption information measuring method of scattering medium according to the present invention is a method comprising: (a) making modulated light having a predetermined modulation frequency component, incident in a spot shape to a surface of a scattering medium being a measured object; (b) receiving said modulated light having propagated inside the measured object at a plurality of timings and/or at a plurality of positions in the surface of said scattering medium to acquire measurement signals each thereat; (c) detecting signals of said modulation frequency component each from said measurement signals; (d) obtaining cosine components and inclinations of sine component against modulation angular frequency, of the signals of said modulation frequency component obtained in respective measurements at said plurality of timings and/or at said plurality of positions; and (e) based on a predetermined relation among said cosine components, said inclinations of sine component against modulation angular frequency, and a difference between absorption coefficients at said plurality of timings and/or at said plurality of positions, calculating said difference between absorption coefficients being primary information.

Further, a third absorption information measuring method of scattering medium according to the present invention is a method comprising: (a) making modulated light having a predetermined modulation frequency component, incident in a spot shape to a surface of a scattering medium being a measured object; (b) receiving said modulated light having propagated inside the measured object at a plurality of timings and/or at a plurality of positions in the surface of said scattering medium to acquire measurement signals each thereat; (c) detecting signals of said modulation frequency component each from said measurement signals; (d) obtaining amplitudes and inclinations of phase against modulation angular frequency, of the signals of said modulation frequency component obtained in respective measurements at said plurality of timings and/or at said plurality of positions; and (e) based on a predetermined relation among said amplitudes, said inclinations of phase against modulation angular frequency, and a difference between absorption coefficients at said plurality of timings and/or at said plurality of positions, calculating said difference between absorption coefficients being primary information.

Yet further, a fourth absorption information measuring method of scattering medium according to the present invention is a method comprising: (a) making modulated light having a predetermined modulation frequency component, incident in a spot shape to a surface of a scattering medium being a measured object; (b) receiving said modulated light having propagated inside the measured object at a plurality of timings and/or at a plurality of positions in the surface of said scattering medium to acquire measurement signals each thereat; (c) detecting signals of said modulation frequency component each from said measurement signals; (d) obtaining phases and inclinations of natural logarithm of amplitude against modulation angular frequency, of the signals of said modulation frequency component obtained in respective measurements at said plurality of timings and/or at said plurality of positions; and (e) based on a predetermined relation among said phases, said inclinations of natural logarithm of amplitude against modulation angular frequency, and a difference between absorption coefficients at said plurality of timings and/or at said plurality of positions, calculating said difference between absorption coefficients being primary information.

In the above methods of the present invention, using the difference between absorption coefficients obtained as described above, a difference of concentration of an absorptive constituent can be quantified based on a predetermined relation among this difference between absorption coefficients, an absorption coefficient per unit concentration of the absorptive constituent, and the difference of concentration of the absorptive constituent.

In the methods of the present invention modulated light having a plurality of wavelengths may be used. Specifically, a fifth absorption information measuring method of scattering medium according to the present invention is a method comprising: (a) making a plurality of modulated light beams having a predetermined modulation frequency component and having different wavelengths at which scattering coefficients of a measured object are substantially equal to each other (equal to each other or regarded as equal to each other), incident in a spot shape to a surface of a scattering medium being the measured object; (b) receiving said modulated light beams having propagated inside the measured object at a predetermined position in the surface of said scattering medium to acquire measurement signals for said respective wavelengths; (c) detecting signals of said modulation frequency component each from said measurement signals; (d) obtaining sine components and an inclinations of cosine component against modulation angular frequency, of the signals of said modulation frequency component obtained for said respective wavelengths; and (e) based on a predetermined relation among said sine components, said inclinations of cosine component against modulation angular frequency, and a difference between absorption coefficients at said respective wavelengths, calculating said difference between absorption coefficients being primary information.

Also, a sixth absorption information measuring method of scattering medium according to the present invention is a method comprising: (a) making a plurality of modulated light beams having a predetermined modulation frequency component and having different wavelengths at which scattering coefficients of a measured object are substantially equal to each other (equal to each other or regarded as equal to each other), incident in a spot shape to a surface of a scattering medium being the measured object; (b) receiving said modulated light beams having propagated inside the measured object at a predetermined position in the surface of said scattering medium to acquire measurement signals for said respective wavelengths; (c) detecting signals of said modulation frequency component each from said measurement signals; (d) obtaining cosine components and inclinations of sine component against modulation angular frequency, of the signals of said modulation frequency component obtained for said respective wavelengths; and (e) based on a predetermined relation among said cosine components, said inclinations of sine component against modulation. angular frequency, and a difference between absorption coefficients at said respective wavelengths, calculating said difference between absorption coefficients being primary information.

Further, a seventh absorption information measuring method of scattering medium according to the present invention is a method comprising: (a) making a plurality of modulated light beams having a predetermined modulation frequency component and having different wavelengths at which scattering coefficients of a measured object are substantially equal to each other (equal to each other or regarded as equal to each other), incident in a spot shape to a surface of a scattering medium being the measured object; (b) receiving said modulated light beams having propagated inside the measured object at a predetermined position in the surface of said scattering medium to acquire measurement signals for said respective wavelengths; (c) detecting signals of said modulation frequency component each from said measurement signals; (d) obtaining amplitudes and inclinations of a phase against modulation angular frequency, of the signals of said modulation frequency component obtained for said respective wavelengths; and (e) based on a predetermined relation among said amplitudes, said inclinations of phase against modulation angular frequency, and a difference between absorption coefficients at said respective wavelengths, calculating said difference between absorption coefficients being primary information.

Yet further, an eighth absorption information measuring method of scattering medium according to the present invention is a method comprising: (a) making a plurality of modulated light beams having a predetermined modulation frequency component and having different wavelengths at which scattering coefficients of a measured object are substantially equal to each other (equal to each other or regarded as equal to each other), incident in a spot shape to a surface of a scattering medium being the measured object; (b) receiving said modulated light beams having propagated inside the measured object at a predetermined position in the surface of said scattering medium to acquire measurement signals for said respective wavelengths; (c) detecting signals of said modulation frequency component each from said measurement signals; (d) obtaining phases and inclinations of natural logarithm of amplitude against modulation angular frequency, of the signals of said modulation frequency component obtained for said respective wavelengths; and (e) based on a predetermined relation among said phases, said inclinations of natural logarithm of amplitude against modulation angular frequency, and a difference between absorption coefficients at said respective wavelengths, calculating said difference between absorption coefficients being primary information.

In the above methods of the present invention using the modulated light having the plurality of wavelengths, using the difference between absorption coefficients obtained as described above, a concentration of an absorptive constituent can be quantified based on a predetermined relation among this difference between absorption coefficients, absorption coefficients per unit concentration of the absorptive constituent at the respective wavelengths, and the concentration of the absorptive constituent. Said measurement signals may be also a plurality of measurement signals obtained when the light beams are received at a plurality of positions in the surface of said measured object.

A first absorption information measuring apparatus of scattering medium according to the present invention is an apparatus comprising: (i) a light incidence section for making modulated light having a predetermined modulation frequency component, incident in a spot shape to a surface of a scattering medium being a measured object; (ii) a photodetection section for receiving said modulated light having propagated inside the measured object at a plurality of timings and/or at a plurality of positions in the surface of said scattering medium to acquire measurement signals each thereat; (iii) a signal detecting section for detecting signals of said modulation frequency component each from said measurement signals; (iv) a first arithmetic section for calculating sine components and inclinations of cosine component against modulation angular frequency, of the signals of said modulation frequency component obtained in respective measurements at said plurality of timings and/or at said plurality of positions; and (v) a second arithmetic section for, based on a predetermined relation among said sine components, said inclinations of cosine component against modulation angular frequency, and a difference between absorption coefficients at said plurality of timings and/or at said plurality of positions, calculating said difference between absorption coefficients being primary information.

Also, a second absorption information measuring apparatus of scattering medium according to the present invention is an apparatus comprising: (i) a light incidence section for making modulated light having a predetermined modulation frequency components incident in a spot shape to a surface of a scattering medium being a measured object; (ii) a photodetection section for receiving said modulated light having propagated inside the measured object at a plurality of timings and/or at a plurality of positions in the surface of said scattering medium to acquire measurement signals each thereat; (iii) a signal detecting section for detecting signals of said modulation frequency component each from said measurement signals; (iv) a first arithmetic section for calculating cosine components and inclinations of sine component against modulation angular frequency, of the signals of said modulation frequency component obtained in respective measurements at said plurality of timings and/or at said plurality of positions; and (v) a second arithmetic section for, based on a predetermined relation among said cosine components, said inclinations of sine component against modulation angular frequency, and a difference between absorption coefficients at said plurality of timings and/or at said plurality of positions, calculating said difference between absorption coefficients being primary information.

Further, a third absorption information measuring apparatus of scattering medium according to the present invention is an apparatus comprising: (i) a light incidence section for making modulated light having a predetermined modulation frequency component, incident in a spot shape to a surface of a scattering medium being a measured object; (ii) a photodetection section for receiving said modulated light having propagated inside the measured object at a plurality of timings and/or at a plurality of positions in the surface of said scattering medium to acquire measurement signals each thereat; (iii) a signal detecting section for detecting signals of said modulation frequency component each from said measurement signals; (iv) a first arithmetic section for calculating amplitudes and inclinations of phase against modulation angular frequency, of the signals of said modulation frequency component obtained in respective measurements at said plurality of timings and/or at said plurality of positions; and (v) a second arithmetic section for, based on a predetermined relation among said amplitudes, said inclinations of phase against modulation angular frequency, and a difference between absorption coefficients at said plurality of timings and/or at said plurality of positions, calculating said difference between absorption coefficients being primary information.

Yet further, a fourth absorption information measuring apparatus of scattering medium according to present invention is an apparatus comprising: (i) a light incidence section for making modulated light having a predetermined modulation frequency component, incident in a spot shape to a surface of a scattering medium being a measured object; (ii) a photodetection section for receiving said modulated light having propagated inside the measured object at a plurality of timings and/or at a plurality of positions in the surface of said scattering medium to acquire measurement signals each thereat; (iii) a signal detecting section for detecting signals of said modulation frequency component each from said measurement signals; (iv) a first arithmetic section for calculating phases and inclinations of natural logarithm of amplitude against modulation angular frequency, of the signals of said modulation frequency component obtained in respective measurements at said plurality of timings and/or at said plurality of positions; and (v) a second arithmetic section for, based on a predetermined relation among said phases, said inclinations of natural logarithm of amplitude against modulation angular frequency, and a difference between absorption coefficients at said plurality of timings and/or at said plurality of positions, calculating said difference between absorption coefficients being primary information.

In the second arithmetic section of the above apparatus according to the present invention, using the difference between absorption coefficients obtained as described above, a difference of concentration of an absorptive constituent can be calculated based on a predetermined relation among this difference between absorption coefficients, an absorption coefficient per unit concentration of the absorptive constituent, and the difference of concentration of the absorptive constituent.

The apparatus of the present invention may be also those using the modulated light having a plurality of wavelengths. Specifically, a fifth absorption information measuring apparatus of scattering medium according to the present invention is an apparatus comprising: (i) a light incidence section for making a plurality of modulated light beams having a predetermined modulation frequency component and having different wavelengths at which scattering coefficients of a measured object are substantially equal to each other (equal to each other or regarded as equal to each other), incident in a spot shape to a surface of a scattering medium being the measured object; (ii) a photodetection section for receiving said modulated light beams having propagated inside the measured object at a predetermined position in the surface of said scattering medium to acquire measurement signals for said respective wavelengths; (iii) a signal detecting section for detecting signals of said modulation frequency component each from said measurement signals; (iv) a first arithmetic section for calculating sine components and inclinations of cosine component against modulation angular frequency, of the signals of said modulation frequency component obtained for said respective wavelengths; and (v) a second arithmetic section for, based on a predetermined relation among said sine components, said inclinations of cosine component against modulation angular frequency, and a difference between absorption coefficients at said respective wavelengths, calculating said difference between absorption coefficients being primary information.

Also, a sixth absorption information measuring apparatus of scattering medium according to the present invention is an apparatus comprising: (i) a light incidence section for making a plurality of modulated light beams having a predetermined modulation frequency component and having different wavelengths at which scattering coefficients of a measured object are substantially equal to each other (equal to each other or regarded as equal to each other), incident in a spot shape to a surface of a scattering medium being the measured object; (ii) a photodetection section for receiving said modulated light beams having propagated inside the measured object at a predetermined position in the surface of said scattering medium to acquire measurement signals for said respective wavelengths; (iii) a signal detecting section for detecting signals of said modulation frequency component each from said measurement signals; (iv) a first arithmetic section for calculating cosine components and inclinations of sine component against modulation angular frequency, of the signals of said modulation frequency component obtained for said respective wavelengths; and (v) a second arithmetic section for, based on a predetermined relation among said cosine components, said inclinations of sine component against modulation angular frequency, and a difference between absorption coefficients at said respective wavelengths, calculating said difference between absorption coefficients being primary information.

Further, a seventh absorption information measuring apparatus of scattering medium according to the present invention is an apparatus comprising: (i) a light incidence section for making a plurality of modulated light beams having a predetermined modulation frequency component and having different wavelengths at which scattering coefficients of a measured object are substantially equal to each other (equal to each other or regarded as equal to each other), incident in a spot shape to a surface of a scattering medium being the measured object; (ii) a photodetection section for receiving said modulated light beams having propagated inside the measured object at a predetermined position in the surface of said scattering medium to acquire measurement signals for said respective wavelengths; (iii) a signal detecting section for detecting signals of said modulation frequency component each from said measurement signals; (iv) a first arithmetic section for calculating amplitudes and inclinations of phase against modulation angular frequency, of the signals of said modulation frequency component obtained for said respective wavelengths; and (v) a second arithmetic section for, based on a predetermined relation among said amplitudes, said inclinations of phase against modulation angular frequency, and a difference between absorption coefficients at said respective wavelengths, calculating said difference between absorption coefficients being primary information.

Yet further, an eighth absorption information measuring apparatus of scattering medium according to the present invention is an apparatus comprising: (i) a light incidence section for making a plurality of modulated light beams having a predetermined modulation frequency component and having different wavelengths at which scattering coefficients of a measured object are substantially equal to each other (equal to each other or regarded as equal to each other), incident in a spot shape to a surface of a scattering medium being the measured object; (ii) a photodetection section for receiving said modulated light beams having propagated inside the measured object at a predetermined position in the surface of said scattering medium to acquire measurement signals for said respective wavelengths; (iii) a signal detecting section for detecting signals of said modulation frequency component each from said measurement signals; (iv) a first arithmetic section for calculating phases and inclinations of natural logarithm of amplitude against modulation angular frequency, of the signals of said modulation frequency component obtained for said respective wavelengths; and (v) a second arithmetic section for, based on a predetermined relation among said phases, said inclinations of natural logarithm of amplitude against modulation angular frequency, and a difference between absorption coefficients at said respective wavelengths, calculating said difference between absorption coefficients being primary information.

In the second arithmetic section of the above apparatus of the present invention using the modulated light having the plurality of wavelengths, using the difference between absorption coefficients obtained as described above, a concentration of an absorptive constituent can be quantified based on a predetermined relation among this difference between absorption coefficients, absorption coefficients per unit concentration of the absorptive constituent at the respective wavelengths, and the concentration of the absorptive constituent. Also, the photodetection section may comprise a light receiving section capable of receiving the light beams at each of plural positions in the surface of the measured object and in this case, it becomes possible to use a plurality of measurement signals obtained when the light beams are received at each of the plural positions in the surface of the measured object, as the aforementioned measurement signals.

The present invention will be more fully understood from the detailed description given hereinbelow and the accompanying drawings, which are given by way of illustration only and are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will be apparent to those skilled in the art from this detailed description.

DESCRIPTION OF THE PREFERRED EMBODIMENTS

Principle of the Present Invention

First described is the principle of the present invention. The knowledge described below is one first disclosed by the present inventor.

Various constituents in a living tissue are mixed microscopically inhomogeneously, i.e., are localized. However, considering the spectral analysis of living tissue from the medical and biological viewpoints, most cases are satisfied by quantifying a specific constituent contained in the living tissue from an optical characteristic in the macroscopic view of complex living tissue, i.e., from a measurement value measured as a mean value. This idea is seen in the impulse response and system function of a black box in the linear system theory. Let us consider an example involving a homogeneous scattering medium in which, light is made incident to a surface thereof, light having propagated inside the scattering medium is received at another position to obtain a measurement signal, and a concentration of an absorptive constituent contained inside is quantified from the measurement signal. In this case, the contours of the scattering medium are assumed to be those having non-reentrant surfaces; that is, the medium is of an arbitrary shape that keeps diffuse light emerging from the medium from reentering the medium. Further, the incident light is assumed to be one having an arbitrary time-resolved waveform. In this case, the incident light of the arbitrary time-resolved waveform can be expressed, as apparent from the Fourier transform principle, by superposition of light components modulated at various frequencies, and thus the following discussion will be given in the frequency aspect, considering the incident light of an arbitrary modulation frequency.

Figure 1:
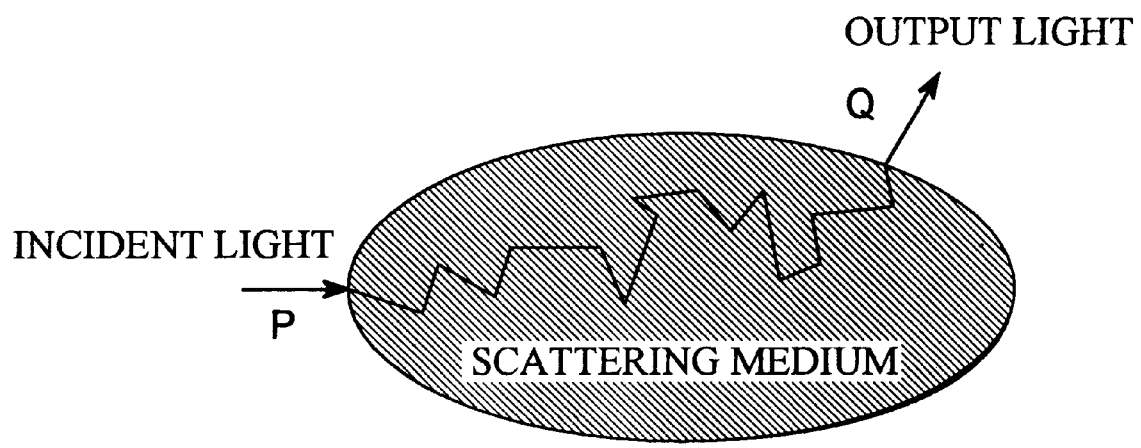
FIG. 1 is a schematic diagram to show the track of the photon having propagated inside the scattering medium.

FIG. 1 shows an example track of a detected photon which has propagated inside a scattering medium or a scattering absorptive body. The light is strongly scattered by scattering constituents, so that the optical path of the photon is bent in a zig-zag pattern. At this time the Lambert-Beer's law holds for the zig-zag flight pathlength and the intensity of propagating light is exponentially attenuated against the zig-zag flight pathlength (cumulative length). Namely, the flight pathlength (optical pathlength) is given by l=ct, where c is the velocity of light in the medium and t is the time of flight, and the survival rate of the photon is given by $\exp(-c\mu_a t)$, where $\mu_a$ is the absorption coefficient. When the light (light beam) is incident at position P and is detected at position Q, photons having passed through various optical paths are detected, and the quantity of detected light being the sum of those photons, which is the survival rate, is proportional to $\exp(-c\mu_a t)$.

Accordingly, light output h(t) obtained with incidence of impulse light into the scattering medium, which is the impulse response, is given as follows.

$$h(t) = J(\mu_s, \mu_a, t) = s(\mu_s, t)\exp(-c\mu_a t) \tag{1.1}$$

$$\ln J(\mu_s, \mu_a, t) = \ln s(\mu_s, t) - c\mu_a t \tag{1.2}$$

$$\frac{\partial}{\partial \mu_a} \ln J(\mu_s, \mu_a, t) = -ct = -l \tag{1.3}$$

Here, J is a term representing the impulse response or output light, $s(\mu_s, t)$ is a term representing a response when the absorption coefficient $\mu_a=0$ (which is a response where only scattering exists), and the exponent term $\exp(-c\mu_a t)$ a term representing attenuation due to the absorption coefficient $\mu_a$. All functions are time-causal functions which become zero when t<0. Further, $\mu_s$ is the scattering coefficient.

The Fourier transform of impulse response h(t) indicates the system function. Considering the Fourier transform of Eq. (1.1) while taking into consideration that the impulse response h(t) is the time-causal function, we can derive the following system function $H(\omega)$.

$$\begin{aligned} H(\omega) &= H(\mu_s, \mu_a, \omega) \\ &= \int_0^\infty h(t)\exp(-j\omega t)dt \\ &= R(c\mu_a, \omega) + jX(c\mu_a, \omega) \\ &= A(c\mu_a, \omega)\exp[j\phi(c\mu_a, \omega)] \end{aligned} \tag{2}$$

Here, $R(c\mu_a, \omega)$ and $X(c\mu_a, \omega)$ are the real part (sine component) and the imaginary part (cosine component), respectively, and $A(c\mu_a, \omega)$ and $\phi(c\mu_a, \omega)$ are the amplitude and phase, respectively. A phase delay is the phase with the opposite sign.

Then substituting Eq. (1.1) into Eq. (2) and arranging it, the following equations are derived. These equations are called as the Cauchy-Riemann equations in the complex function theory.

$$\frac{\partial R(c\mu_a, \omega)}{\partial c\mu_a} = \frac{\partial X(c\mu_a, \omega)}{\partial \omega} \tag{3.1}$$

$$\frac{\partial R(c\mu_a, \omega)}{\partial \omega} = -\frac{\partial X(c\mu_a, \omega)}{\partial c\mu_a} \tag{3.2}$$

It can be further proved that the following relations also hold when Eq. (3.1) and Eq. (3.2) hold.

$$\frac{\partial \ln A(c\mu_a, \omega)}{\partial c\mu_a} = \frac{\partial \phi(c\mu_a, \omega)}{\partial \omega} \tag{4.1}$$

$$\frac{\partial \ln A(c\mu_a, \omega)}{\partial \omega} = -\frac{\partial \phi(c\mu_a, \omega)}{\partial \omega}. \tag{4.2}$$

For calculating the absorption coefficient $\mu_a$, which is the primary object of the present invention, either one of Eqs. (3.1) to (4.2) may be used. Specifically, it is preferred to use integrations of these equations over $\mu_a$, i.e., the following equations obtained from the above equations.

$$R(c\mu_a, \omega) = c\int_0^{\mu_a} \frac{\partial X(c\mu_a, \omega)}{\partial \omega} d\mu_a + R(0, \omega), \tag{5.1}$$

$$X(c\mu_a, \omega) = -c\int_0^{\mu_a} \frac{\partial R(c\mu_a, \omega)}{\partial \omega} d\mu_a + X(0, \omega), \tag{5.2}$$

$$\ln A(c\mu_a, \omega) = c\int_0^{\mu_a} \frac{\partial \phi(c\mu_a, \omega)}{\partial \omega} d\mu_a + \ln A(0, \omega), \tag{5.3}$$

$$\phi(c\mu_a, \omega) = -c\int_0^{\mu_a} \frac{\partial \ln A(c\mu_a, \omega)}{\partial \omega} d\mu_a + \phi(0, \omega). \tag{5.4}$$

Here, the second terms in the right sides of Eqs. (5.1) to (5.4) are integration constants, each of which indicates a value at $\mu_a=0$. Described below are methods for calculating information concerning absorption from measured values by use of Eqs. (5.1) to (5.4).

(Measurements of concentration change of absorptive constituent)

Let us consider a case wherein a medium contains one type of absorptive constituent and the absorption coefficient $\mu_a$ thereof has changed from $\mu_{a1}$ to $\mu_2$ with change in the concentration thereof. Supposing Eqs. (5.1) to (5.4) hold before and after the change and $s(\mu_s, t)$ is invariant before and after the change, the following equations are derived using $\mu_{a1}$ and $\mu_{a2}$ before and after the change.

$$R(c\mu_{a2}, \omega) - R(c\mu_{a1}, \omega) = c\int_{\mu_{a1}}^{\mu_{a2}} \frac{\partial X(c\mu_a, \omega)}{\partial \omega} d\mu_a, \tag{6.1}$$

$$X(c\mu_{a2}, \omega) - X(c\mu_{a1}, \omega) = -c\int_{\mu_{a1}}^{\mu_{a2}} \frac{\partial R(c\mu_a, \omega)}{\partial \omega} d\mu_a, \tag{6.2}$$

$$\ln \frac{A(c\mu_{a2}, \omega)}{A(c\mu_{a1}, \omega)} = c\int_{\mu_{a1}}^{\mu_{a2}} \frac{\partial \phi(c\mu_a, \omega)}{\partial \omega} d\mu_a, \tag{6.3}$$

$$\phi(c\mu_{a2}, \omega) - \phi(c\mu_{a1}, \omega) = -c\int_{\mu_{a1}}^{\mu_{a2}} \frac{\partial \ln A(c\mu_a, \omega)}{\partial \omega} d\mu_a. \tag{6.4}$$

With normal scattering media the scattering characteristics may be considered not to change with change in the concentration of absorptive constituent. This is just as if ink is mixed in milk.

Next applying the mean value theorem, the following equations are obtained from Eqs. (6.1) to (6.4).

$$R(c\mu_{a2}, \omega) - R(c\mu_{a1}, \omega) \approx c(\mu_{a2} - \mu_{a1})\frac{\partial X(c\mu_a, \omega)}{\partial \omega}\bigg|_{\mu_{x1}}, \tag{7.1}$$

$$X(c\mu_{a2}, \omega) - X(c\mu_{a1}, \omega) \approx -c(\mu_{a2} - \mu_{a1})\frac{\partial R(c\mu_a, \omega)}{\partial \omega}\bigg|_{\mu_{x2}}, \tag{7.2}$$

$$\ln \frac{A(c\mu_{a2}, \omega)}{A(c\mu_{a1}, \omega)} \approx c(\mu_{a2} - \mu_{a1})\frac{\partial \phi(c\mu_a, \omega)}{\partial \omega}\bigg|_{\mu_{x3}}, \tag{7.3}$$

$$\phi(c\mu_{a2}, \omega) - \phi(c\mu_{a1}, \omega) \approx -c(\mu_{a2} - \mu_{a1})\partial \ln \frac{A(c\mu_a, \omega)}{\partial \omega}\bigg|_{\mu_{x4}}. \tag{7.4}$$

Here, $\mu_{xi}$ (i=1, 2, 3, 4) denotes a suitable value satisfying the condition of $\mu_{a1} \leq \mu_{xi} \leq \mu_{a2}$ or $\mu_{a1} \geq \mu_{xi} \geq \mu_{a2}$.

The above demonstrates that once we know the modulation angular frequency $\omega$ of modulated light used in measurement and inclinations of the four parameters, $\partial X/\partial \omega$, $\partial R/\partial \omega$, $\partial \phi/\partial \omega$, $\partial \ln A/\partial \omega$, at $\mu_a=\mu_{xi}$, we can calculate the difference between the absorption coefficients before and after the change, $\mu_{a2}-\mu_{a1}$, from the values of X, R, A, $\phi$ before and after the change (which can be obtained all from observed values) and the value of c determined by the refractive index of the medium and the velocity of light therein.

In the above case, the above inclinations of the four parameters $B_i$ (i=1, 2, 3, 4) at $\mu_a=\mu_{xi}$, $\partial B_i/\partial\omega|_{\mu_{xi}}$, can be expressed as follows by use of the inclinations at $\mu_{a1}$ and at $\mu_{a2}$.

$$\frac{\partial B_i}{\partial \omega}\bigg|_{\mu_{xi}} \approx p_i \frac{\partial B_i}{\partial \omega}\bigg|_{\mu_{a1}} + (1-p_i)\frac{\partial B_i}{\partial \omega}\bigg|_{\mu_{a2}} \tag{8}$$

Here, $p_i$ is a suitable value satisfying the condition of $0 \leq p_i \leq 1$. In this case, since $B_i$ are monotonic functions and the inclinations at $\mu_{a1}$ and at $\mu_{a2}$ are normally nearly equal, $p_i=\frac{1}{2}$ may be assumed.

Further, inclinations of the four parameters at the modulation angular frequency $\omega_1$, $\partial B_i/\partial\omega|_{\omega_1}$, can be measured by use of modulated light having two modulation angular frequency components satisfying $\omega=\omega_1\pm\Delta\omega/2$ (>0). This relation can be expressed by the following equation.

$$\frac{\partial B_i(c\mu_a, \omega)}{\partial \omega}\bigg|_{\omega_1} \approx \frac{B_i(c\mu_a, \omega_1 + \Delta\omega/2) - B_i(c\mu_a, \omega_1 - \Delta\omega/2)}{\Delta\omega} \tag{9}$$

Accordingly, the respective inclinations $\partial B_i/\partial\omega$ of Eqs. (7.1) to (7.4) become as follows when Eq. (9) is substituted into Eq. (8) and $p_i=\frac{1}{2}$.

$$\left.\frac{\partial B_i}{\partial \omega}\right|_{\mu_{zi},\omega_1} \approx \frac{1}{2\Delta\omega}[B_i(c\mu_{a1}, \omega_1 + \Delta\omega/2) + B_i(c\mu_{a2}, \omega_1 + \Delta\omega/2) - \quad (10)$$
$$B_i(c\mu_{a1}, \omega_1 - \Delta\omega/2) - B_i(c\mu_{a2}, \omega_1 - \Delta\omega/2)]$$

The above described the method for precisely obtaining $\partial B_i/\partial \omega$.

On the other hand, it is empirically known that the approximation of $\partial\phi/\partial\omega \approx \phi/\omega$ can be applied at low modulation frequencies (for example, at $f=\omega/2\pi=100$ MHz or less in measurements of living bodies or the like). This can be derived by analyzing the response of a scattering medium having a simple shape by use of the photon diffusion equation. More specifically, boundary conditions are determined for a semi-infinite medium or a medium of a rectangular parallelepiped having a size over a certain level, and the photon diffusion equation is solved under the determined boundary conditions to obtain the inclinations $\partial B_i/\partial\omega$ in the right sides of Eqs. (7.1) to (7.4), whereby the approximate equations of the inclinations $\partial B_i/\partial\omega$ can be derived. For example, in the case of the relation of Eq. (7.3), approximation of $\partial\phi/\partial\omega = \phi/\omega$ holds. Accordingly, at low modulation frequencies, $\partial\phi/\partial\omega = \phi/\omega$ may be applied to Eq. (7.3). In this case, forgoing Eq. (7.3) is changed to the following.

$$\ln\frac{A(c\mu_{a2}, \omega)}{A(c\mu_{a1}, \omega)} \approx c(\mu_{a2} - \mu_{a1})\frac{p\phi(c\mu_{a1}, \omega) + (1-p)\phi(c\mu_{a2}, \omega)}{\omega} \quad (11)$$

Here, p is a coefficient similar to that used in Eq. (8) and $p=\frac{1}{2}$ may be normally assumed herein. It is clear that for foregoing Eqs. (7.1), (7.2), and (7.4), approximate equations corresponding to the respective equations can also be derived in the same manner as above.

For calculating concentration change $\Delta V$ of absorptive constituent, the following equation derived from the Lambert-Beer's law is applied.

$$\epsilon\Delta V = \mu_{a2} - \mu_{a1} \quad (12)$$

Here, $\epsilon$ is an absorption coefficient (or an extinction coefficient) per unit concentration of absorptive constituent, which can be measured by a spectrometer. Changes in concentrations of two or more types of absorptive constituents can also be measured using light having two or more wavelengths by the above method.

The above description clarified the method for measuring the concentration change of absorptive constituent inside the scattering medium from Eqs. (7.1) to (7.4) and Eq. (12). It is also possible to conduct the above measurement using modulated light of different wavelengths. Accordingly, a temporal change of concentration of absorptive constituent in the scattering medium can be measured while fixing the measuring site. This measurement can be applied to measurements of temporal change of concentration of hemoglobin in a certain portion, and the like.

(Measurements of concentration change of absorptive constituent or spatial distribution of concentration difference thereof from reference value)

It is also possible to measure a distribution of temporal change of concentration of absorptive constituent inside the scattering medium by carrying out the above-stated measurement while moving or scanning the measuring site. In addition, it is also possible to measure a distribution of difference of concentration of absorptive constituent inside the scattering medium with respect to a reference value, by moving or scanning the measuring site along a measured object while fixing the positions of light incidence and light reception relative to each other, performing measurements during the movement, and taking a measured value at an arbitrary position as the reference value. Such measurements can be applied to photo-mammography for diagnosis of breast cancer. These measurements according to the present invention can be applied to scattering media of various shapes having non-reentrant contours, and specific application examples include fluoroscopes, optical CT, clinical monitors utilized in surgery or cure, and so on, as well as the photo-mammography. These examples utilize such methods as light reception at multiple points, scanning of light incidence position and light receiving position, and time-sharing measurement as occasion may demand.

(Measurement of concentration of specific absorptive constituent)

The following describes the measurement with modulated light (of modulation angular frequency $\omega$) from light having two wavelengths $\lambda_1$ and $\lambda_2$, i.e., the dual-wavelength spectrophotometry.

First, let us assume that a scattering medium containing one absorptive constituent has the absorption coefficient $\mu_{a1}$ for light of wavelength $\lambda_1$ and $\mu_{a2}$ for light of wavelength $\lambda_2$. It is also assumed that the scattering coefficients of the medium for the light of wavelengths $\lambda_1$ and $\lambda_2$ are equal or nearly equal to each other. Such conditions are realized readily by selecting the wavelengths used in measurement. Under these circumstances, similar equations to Eqs. (6.1) to (6.4) are derived from forgoing Eqs. (5.1) to (5.4). However, the definition of absorption coefficients $\mu_{a1}$ and $\mu_{a2}$ is different from that in the case of Eqs. (6.1) to (6.4) and $\mu_{a1}$ and $\mu_{a2}$ herein mean the absorption coefficients of the measured medium for the light of wavelengths $\lambda_1$ and $\lambda_2$. Further, equations similar to foregoing Eqs. (7.1) to (7.4) are obtained and the difference between the absorption coefficients of the measured medium for the light of the two wavelengths, $\mu_{a2} - \mu_{a1}$, can be obtained by use of these equations.

The concentration V of a specific absorptive constituent is calculated from the below equation, using the absorption coefficients (or extinction coefficients) per unit concentration of the specific absorptive constituent for the light of wavelengths $\lambda_1$ and $\lambda_2$, $\epsilon_1$ and $\epsilon_2$.

$$V(\epsilon_2 - \epsilon_1) = \mu_{a2} - \mu_{a1} \quad (13)$$

Here, values of $\epsilon_1$ and $\epsilon_2$ can be preliminarily measured by the electrometer. Accordingly, the absolute concentration V of absorptive constituent can be measured in the exactly same manner as the aforementioned measurement of concentration change of, absorptive constituent.

Considering the wavelength dependence of scattering coefficient, for example, the equation corresponding to foregoing Eq. (6.3) becomes as follows by use of the scattering coefficients $\mu_{s1}$ and $\mu_{s2}$ of the measured medium for the light of the wavelengths $\lambda_1$ and $\lambda_2$.

$$\ln\frac{A(c\mu_{a2}, \omega)}{A(c\mu_{a1}, \omega)} \approx c\int_{\mu_{a1}}^{\mu_{a2}}\frac{\partial\phi(c\mu_a, \omega)}{\partial\omega}d\mu_a + \ln\frac{b_2}{b_1} + \ln k \quad (14)$$

$$k = \frac{A(\mu_{s2}, 0, \omega)}{A(\mu_{s1}, 0, \omega)}$$

In this equation, however, the wavelength dependence of $\partial\phi/\partial\omega$ is ignored. Further, $b_2/b_1$ is a ratio of intensities of incident light at the wavelengths $\lambda_1$ and $\lambda_2$ and $A(\mu_{s1}, 0, \omega)$ and $A(\mu_{s2}, 0, \omega)$ are values at $\mu_s=0$. By this, the following equation is attained from Eq. (14) as Eq. (7.3) was.

$$\ln\frac{A(c\mu_{a2}, \omega)}{A(c\mu_{a1}, \omega)} \approx c(\mu_{a2} - \mu_{a1})\frac{\partial\phi(c\mu_a, \omega)}{\partial\omega}\bigg|_{\mu_x} + \ln\frac{b_2}{b_1} + \ln k \quad (15)$$

Also in this case, similarly as in Eq. (7.3), $\mu_x$ is a suitable value satisfying the condition of $\mu_{a1} \leq \mu_x \leq \mu_{a2}$ or $\mu_{a1} \geq \mu_x \geq \mu_{a2}$. By setting $b_2/b_1=1$ and $k=1$, this Eq. (15) becomes equal to foregoing Eq. (7.3). The coefficient $b_2/b_1$ can be set to $b_2/b_1=1$ by adjusting the intensity of incident light. It is also possible to estimate the value of $b_2/b_1$ from a measured value of the intensity of light source. Further, $k=\mu'_{s1}/\mu'_{s2}$ can be derived by solving the photon diffusion equation for a medium of a simple shape. Here, $\mu'_{s1}$ and $\mu'_{s2}$ are transport scattering coefficients at the wavelengths $\lambda_1$ and $\lambda_2$, respectively. Accordingly, the difference between the absorption coefficients, $\mu_{a2}-\mu_{a1}$, of the medium containing the specific absorptive constituent for the light of the two wavelengths can be calculated from Eq. (15). Then the concentration V of the specific absorptive constituent can be further calculated from Eq. (13).

If two-point measurements for receiving output light at two positions are carried out in the above dual-wavelength spectrophotometry, a new relation will be attained by eliminating the coefficient $b_2/b_1$ described above. Namely, the coefficient $b_2/b_1$ can be eliminated by utilizing no dependence of the coefficient $b_2/b_1$ on the detection positions. Further, it is a matter of course that the above-stated method can be expanded to multiple-wavelength spectrophotometry using light having three or more wavelengths.

(Measurements of spatial distribution of concentration of absorptive constituent)

The measurement of spatial distribution of concentration of absorptive constituent is achieved by performing the above-stated measurement at multiple points. This measurement according to the present invention enables measurements with the scattering media of various shapes having non-reentrant contours. Specific application examples include the photo-mammography, fluoroscopes, optical CT, and so on. These examples employ the methods such as the light reception at multiple points, scanning of light incidence position and light receiving position, and the time-sharing measurement as occasion may demand. The features of these measurements are the capability of measuring the spatial distribution of concentration of specific absorptive constituent, the spatial distribution of difference between absorptive constituents of the measured medium for the light of two wavelengths, the spatial distribution of temporal change of concentration of specific absorptive constituent, and so on, as described above. These pieces of information are utilized in the clinical monitor, diagnosis or analysis, and surgery or cure.

EMBODIMENTS

Embodiments of the present invention will be described with reference to the accompanying drawings. It is, however, noted that in the following description the same elements will be denoted by the same reference symbols and redundant description will be omitted.

Embodiment 1

Figure 2:
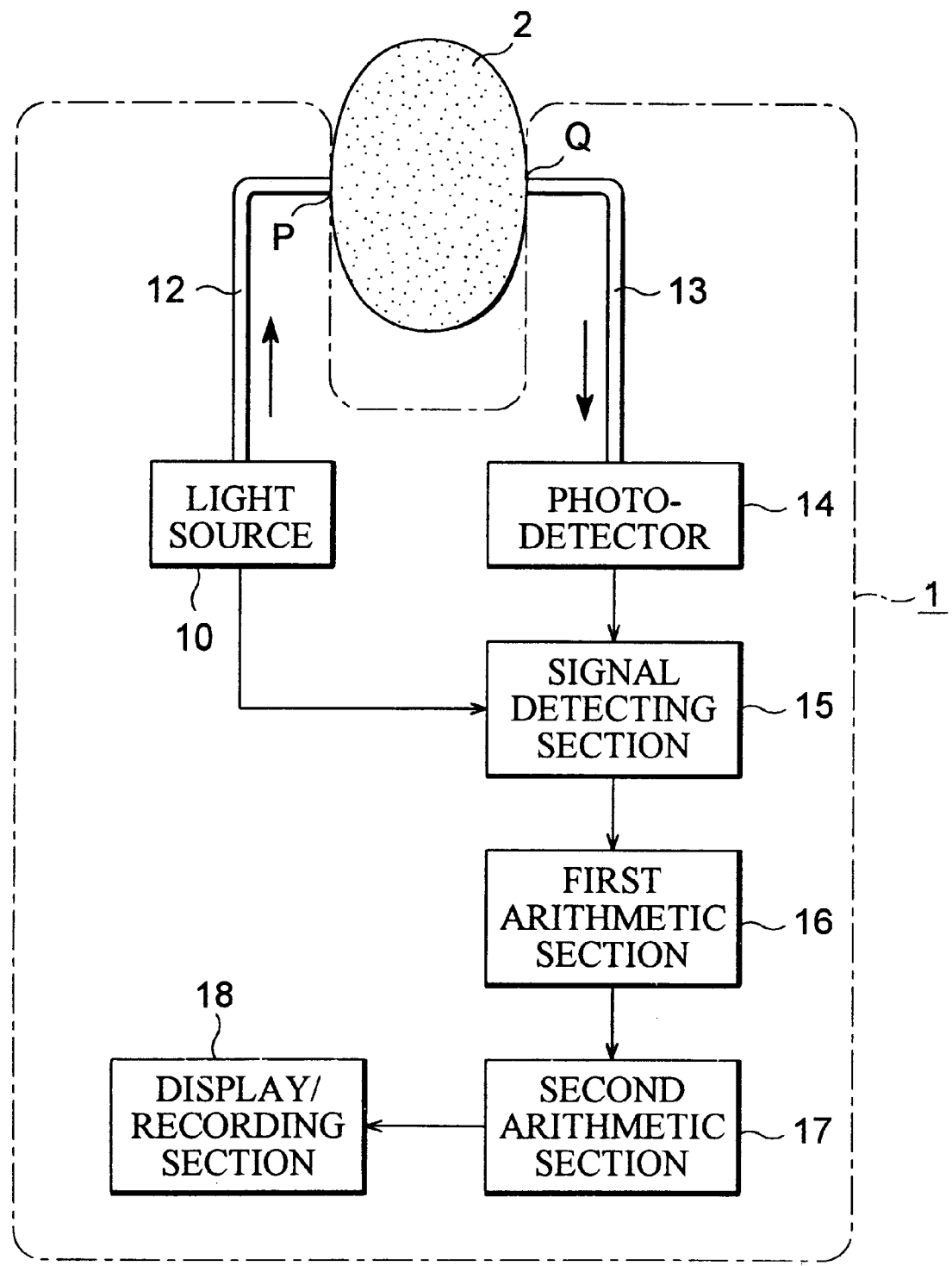
FIG. 2 is a schematic diagram of the configuration of the apparatus in the first embodiment according to the present invention.

FIG. 2 shows the first embodiment of the apparatus of the present invention for carrying out the method of the present invention and illustrates the configuration of apparatus 1 for measuring the temporal change of concentration of absorptive constituent inside scattering medium 2. In this configuration of apparatus 1, modulated light of predetermined wavelength $\lambda$ and modulation frequency f (the modulation angular frequency $\omega=2\pi f$) is made incident on position P (light incidence position) in the surface of scattering medium 2 and the light having propagated inside the scattering medium 2 is received at another position Q (photodetection position) in the surface. Then a change in the concentration of an absorptive constituent inside the scattering medium is quantified by repetitively carrying out measurements. In this case, the change in the concentration of the absorptive constituent can be quantified by taking a concentration of the absorptive constituent in the first measurement as a reference value. The measuring apparatus 1 is integrally housed in one casing.

Figure 3:
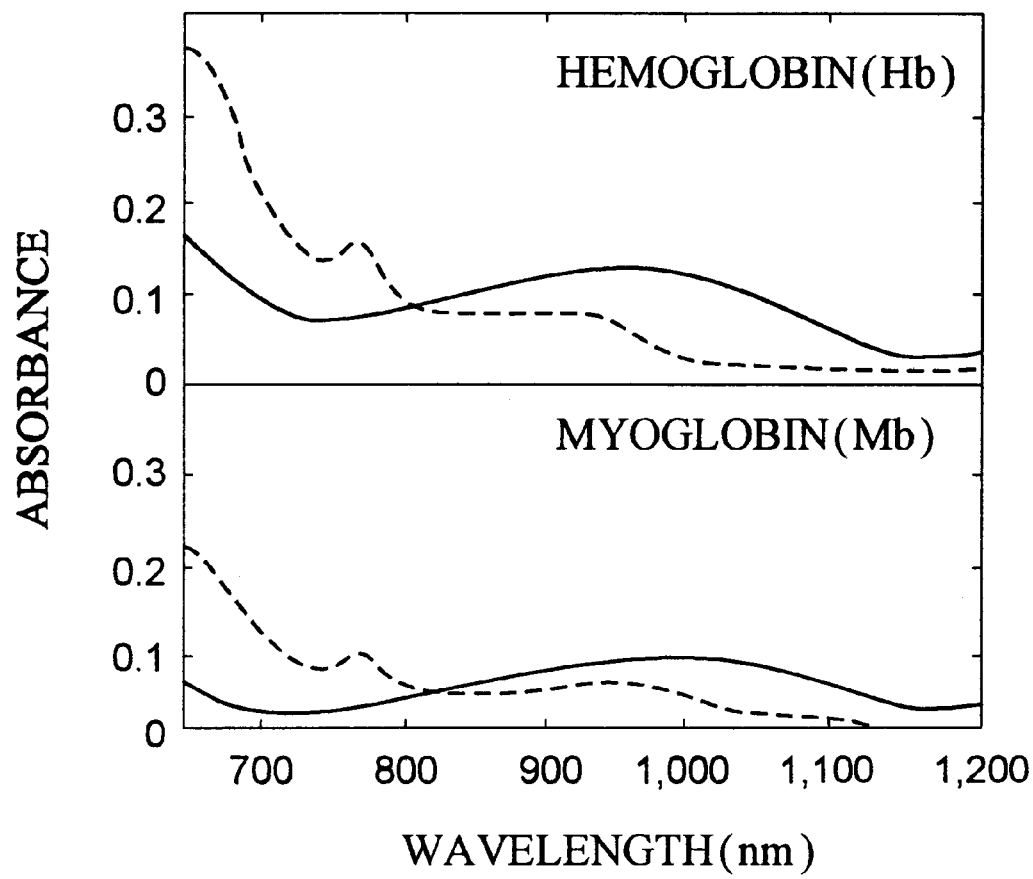
FIG. 3 is a graph to show the absorption spectra of hemoglobin and myoglobin.

A laser diode or the like is used as light source 10, and the modulated light of wavelength $\lambda$ and predetermined modulation angular frequency $\omega$ is generated thereby. In this case, the wavelength is selected depending upon the scattering medium and the absorptive constituent to be measured. In measurements of living body, oxygenated and deoxygenated hemoglobin and oxygenated and deoxygenated myoglobin is often measured and absorption spectra of those absorptive constituents are shown in FIG. 3. Therefore, the light of 600 nm to 1.3 $\mu$m is normally used in the measurements of living body. The modulation frequency f is properly selected in the range of 1 MHz to 1 GHz. This modulation frequency is preferably as high as possible in measurements of spatial distribution. In the following, f=100 MHz. The light source 10 can also be selected from the light-emitting diode, HeNe laser, and so on, as well as the laser diode.

Figure 4A:
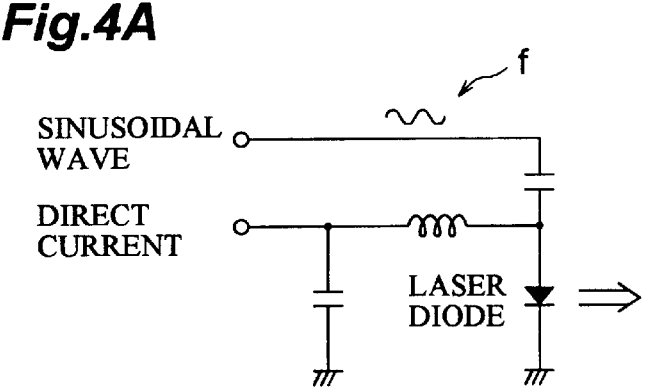
FIGS. 4A, 4C and 4E are schematic diagrams each showing a method for generating sinusoidal modulated light.
Figure 4B:
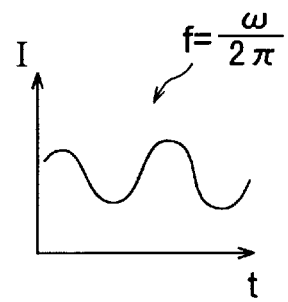
FIGS. 4B, 4D and 4F are schematic diagrams each showing sinusoidal modulated light generated by a method shown in FIGS. 4A, 4C or 4E.
Figure 4C:
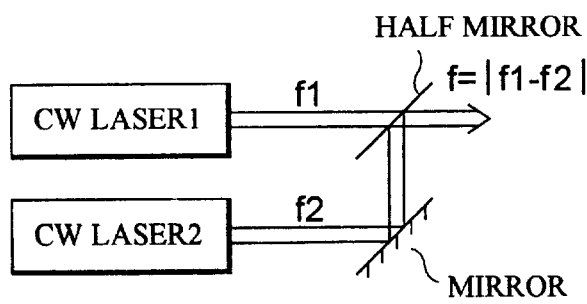
Figure 4D:
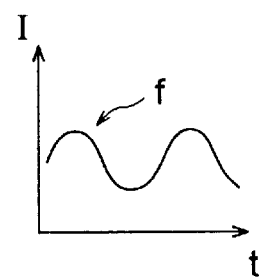
Figure 4E:
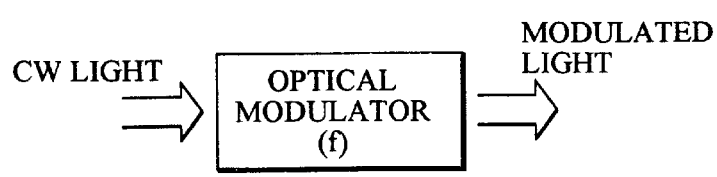
Figure 4F:
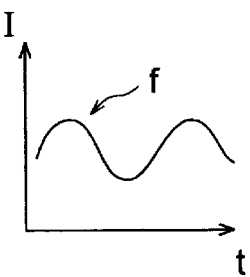

Sinusoidal modulated light of the predetermined angular frequency is generated by current modulation of the laser diode as shown in FIGS. 4A and 4B. The sinusoidal modulated light can also be generated by beat of two cw lasers or by use of an optical modulator, as shown in FIGS. 4C and 4D and in FIGS. 4E and 4F.

The modulated light emitted from the light source 10 is incident through light guide 12 to the surface of scattering medium 2, which is a measured object. The space between the light guide 12 and the scattering medium 2 is very small in the embodiment of FIG. 2. In practice, however, this space may be widened and may be filled with a liquid substance or a jelly substance (which will be called an interface material) having the refractive index and scattering coefficient nearly equal to those of the scattering medium 2. Namely, the modulated light propagates in this interface material to enter the measured object without posing any problem. If reflection on the surface of scattering medium is problematic, influence of the surface reflection or the like can be decreased by properly selecting the interface material.

The modulated light having propagated inside the scattering medium is received by light guide 13 located at position Q the distance r apart from the aforementioned light incidence position P. The interface material may also be employed herein for the same reason as above. Photodetector 14 converts an optical signal of the light received into an electric signal, amplifies it if necessary, and outputs a measurement signal. The photodetector 14 may be selected from a phototube, a photodiode, an avalanche photodiode, a PIN photodiode, and so on, in addition to a photomultiplier tube. In selection of the photodiode, it needs to have the spectral sensitivity characteristics for detecting the light of predetermined wavelengths and necessary time response speed. For weak light signals, a high-gain photodetector is used. Further, the time correlation photon counting method for counting photons may be applied. The other places than the light receiving surface of photodetector are desirably constructed in structure for absorbing or intercepting the light.

Signal detecting section 15 detects a signal of the predetermined modulation frequency component from the aforementioned measurement signal. Specifically, the monodyne detection, heterodyne detection, or lock-in detection, well known, is used. In this case, the signal detecting section 15 utilizes a signal synchronized with the modulated light emitted from the light source 10 as occasion demands. First arithmetic section 16 calculates the amplitude A and the inclination (derivative) $\partial\phi/\partial\phi$ of phase ω against the modulation angular frequency from the foregoing signal of the predetermined modulation frequency component. Then the above measurement is carried out repetitively. Now, let us consider the m-th and (m+1)-th measurements.

Second arithmetic section 17 substitutes two said amplitudes $A_m$ and $A_{m+1}$ obtained in the m-th and (m+1)-th measurements, and an inclination of phase $\partial\phi/\partial\omega|\mu_{x3}$ obtained from two said inclinations of phase into aforementioned Eq. (7.3) to calculate a change amount of absorption coefficient of scattering medium 2, $\mu_{a(m+1)-\mu am}$ (primary information), and further calculates a change amount of absorptive constituent by use of aforementioned Eq. (12).

At this time, for calculating the inclination of phase $\partial\phi/\phi\omega|\mu x3$, aforementioned Eq. (8) is used and sufficient accuracy is achieved with p=½. Since f=100 MHz, the approximation $\partial\phi/\partial\omega\approx\mu/\omega$, may be applied as described above. In the case of f>100 MHz, measurements are conducted with the modulated light of two modulation angular frequencies $\omega=\omega_1\pm\Delta\omega/2$ (>0) and $\partial\phi/\partial\omega|\mu_{x3}$ is calculated using aforementioned Eq. (10). These arithmetic processes are executed at high speed by microcomputers incorporated in the first and second arithmetic sections.

The second arithmetic section 17 has a function to store the concentration information of absorptive constituent thus obtained and display/recording means 18 is a section for displaying or recording these information pieces.

The above arrangement used the modulated light of one wavelength, but modulated light of two or more wavelengths may also be utilized in practice. Further, it is also possible to make the light incident to one position and to detect the propagating light at two or more positions. These may be detected in parallel or in time division.

Figure 5A:
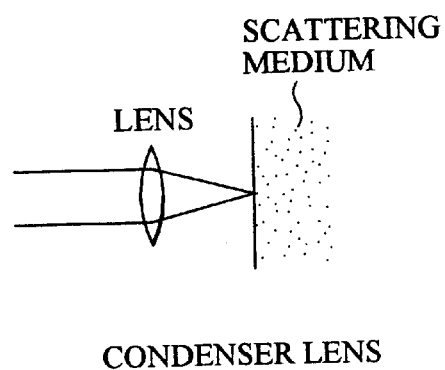
FIGS. 5A, 5B, 5C and 5D are schematic diagrams each showing a light incidence method to the scattering medium.
Figure 5B:
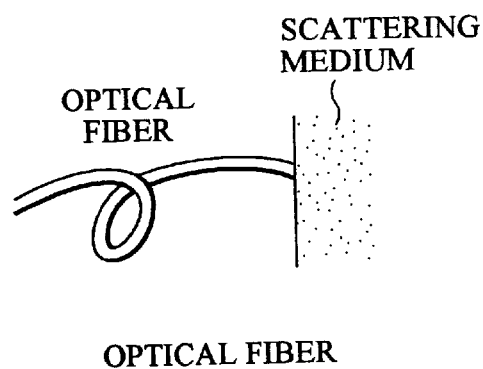
Figure 5C:
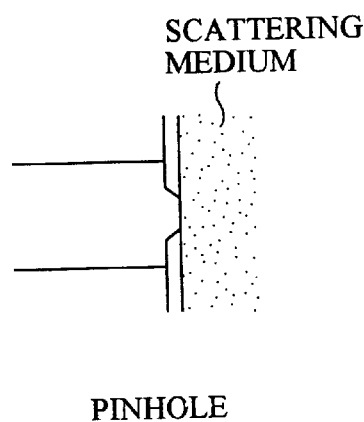
Figure 5D:
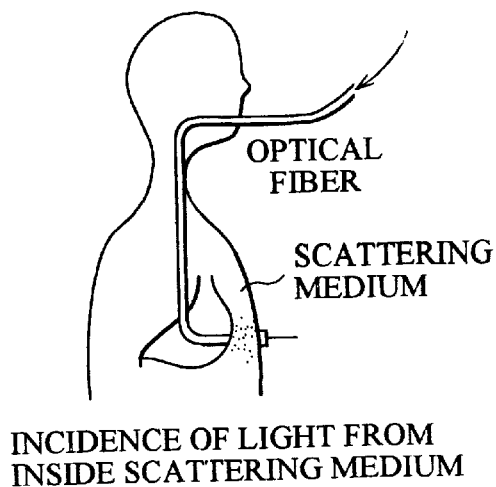

The means for making the light incident to the scattering medium 2, instead of the light guide 12 shown in FIG. 2, may be selected from a method with a condenser lens (FIG. 5A), a method using an optical fiber (FIG. 5B), a method utilizing a pinhole (FIG. 5C), a method for making the light incident from inside a body like a gastrocamera (FIG. 5D), and so on. A thick beam of light may also be made incident to the scattering medium 2. In this case, the light source may be regarded as an array of plural spot light sources.

Figure 6A:
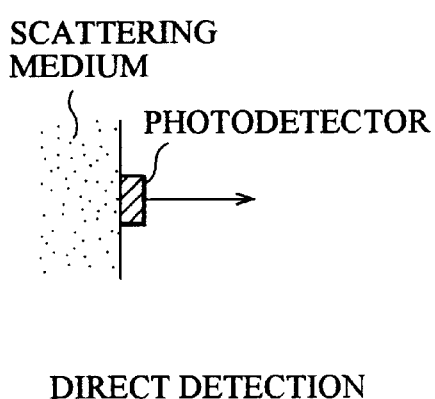
FIGS. 6A, 6B and 6C are schematic diagrams each showing a light receiving method.
Figure 6B:
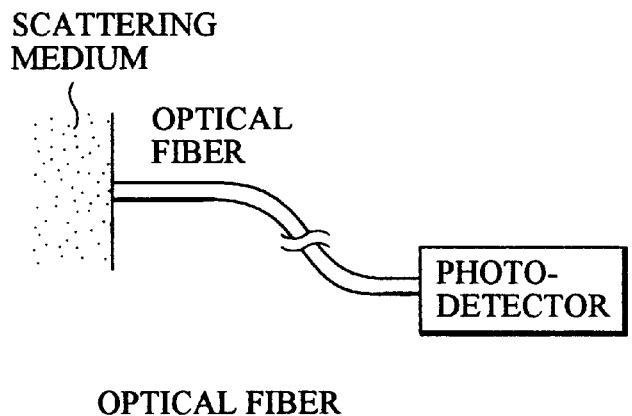
Figure 6C:
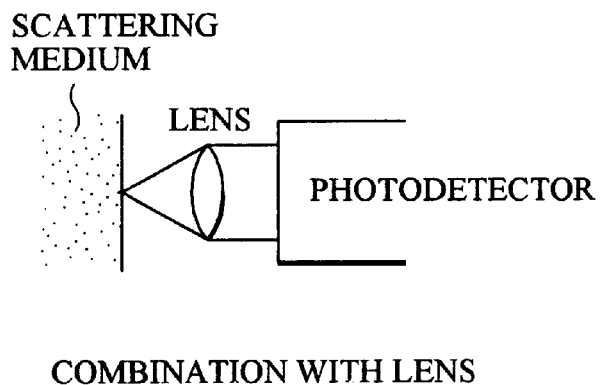

The means for detecting the light having diffuse-propagated inside the scattering medium 2, other than the method using the light guide 13 shown in FIG. 2, may be selected from a method for directly detecting it (FIG. 6A), a method using an optical fiber (FIG. 6B), a method using a lens (FIG. 6C), and so on.

The above first arithmetic section 16 was described as to the case for calculating the amplitude A and inclination $\partial\phi/\partial\omega$ of phase φ against modulation angular frequency from the signal of the predetermined modulation frequency component. However, it may also calculate from the signal of the predetermined modulation frequency component either one combination of (i) the sine component with the inclination (derivative) of cosine component against modulation angular frequency, (ii) the cosine component with the inclination (derivative) of sine component against modulation angular frequency, or (iii) the phase with the inclination (derivative) of natural logarithm of amplitude against modulation angular frequency, as described previously. In that case, "amplitude A, inclination $\partial\phi/\partial\omega$ phase φ against modulation angular frequency, and Eq. (7.3)" in above Embodiment 1 should read (i) "sine component, inclination (derivative) of cosine component against modulation angular frequency, and Eq. (7.1)," (ii) "cosine component, inclination (derivative) of sine component against modulation angular frequency, and Eq. (7.2)," or (iii) "phase, inclination (derivative) of natural logarithm of amplitude against modulation angular frequency, and Eq. (7.4)." Accordingly, the first embodiment stated herein can quantify the change of concentration of absorptive constituent according to Eqs. (7.1) to (7.4).

Embodiment 2

Measurements are carried out in the same manner as in above Embodiment 1 except for synchronous scanning of the light incidence position P and photodetection position Q of the modulated light relative to the scattering medium 2, and the reference value is a concentration of the absorptive constituent at an arbitrary position, whereby a spatial distribution of concentration difference from the reference value can be measured. Also in this case, similarly as in above Embodiment 1, the spatial distribution of difference of concentration of absorptive constituent from the reference value can be measured using Eqs. (7.1) to (7.4).

Figure 7:
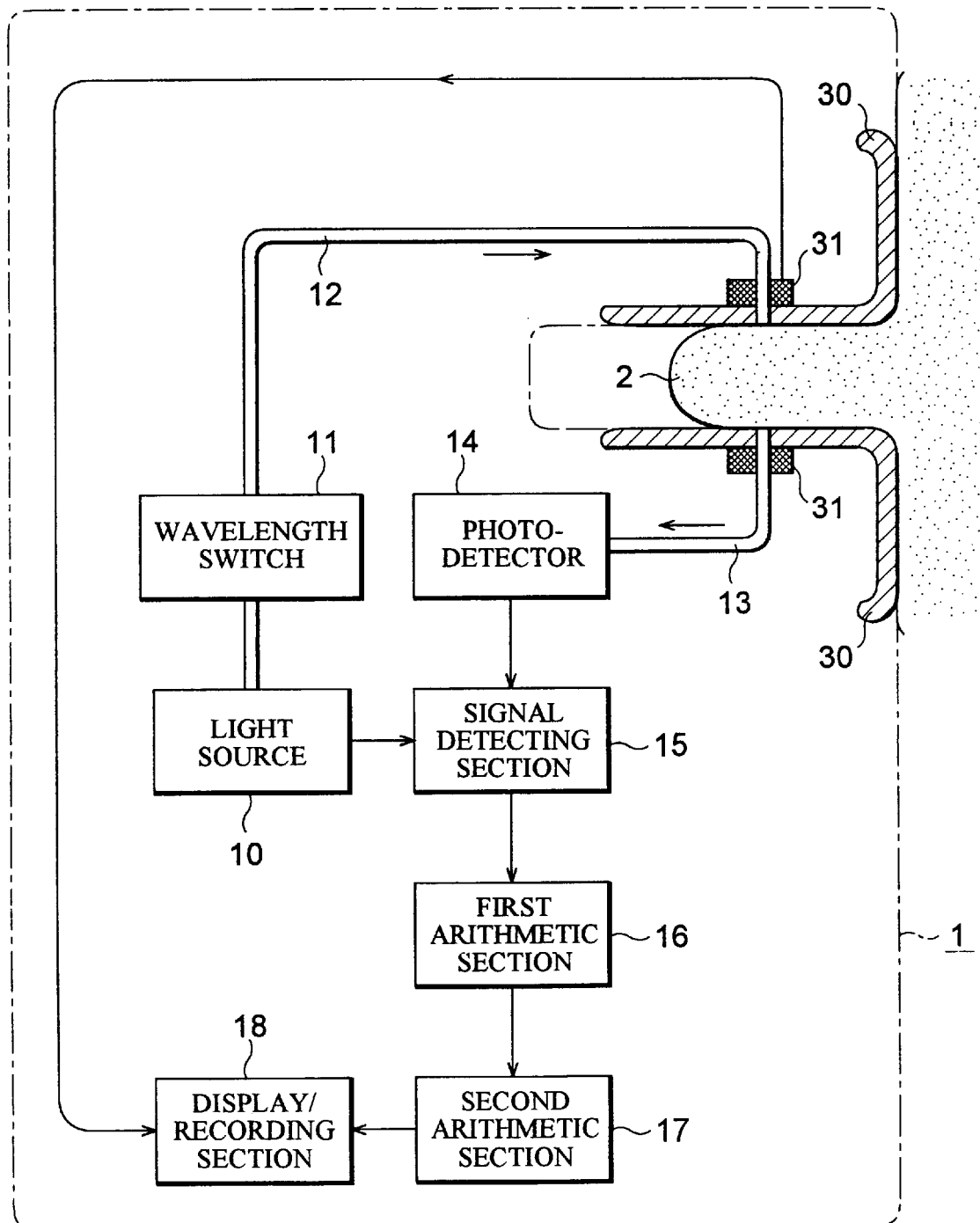
FIG. 7 is a schematic diagram of the configuration of the apparatus in the second embodiment according to the present invention.

FIG. 7 shows the second embodiment of the apparatus of the present invention for carrying out the method of the present invention and illustrates the configuration of apparatus 1 (mammography) for measuring the spatial distribution of concentration of absorptive constituent inside the scattering medium 2 like the breast. In FIG. 7 the components having the same functions as those shown in FIG. 2 associated with the aforementioned first embodiment are denoted by the same symbols. The modulated light of predetermined wavelength λ and modulation frequency f (the modulation angular frequency ω=2πf) is made incident to the surface of scattering medium 2 and the light having propagated inside the scattering medium is received at the position in the surface on the opposite side. On this occasion, the measurement is conducted while synchronously moving the incidence position and photodetection position of the modulated light. Then, for example, using a concentration of the absorptive constituent in the measurement at the first position (the first light incidence position and first photodetection position) as the reference value, the spatial distribution of concentration difference of absorptive constituent can be measured.

The apparatus 1 shown in FIG. 7 associated with the second embodiment has first mechanical section 30 for lightly nipping the scattering medium 2 in parallel. Namely, the first mechanical section 30 enables the scattering medium 2 like the breast to be measured in a slightly flattened state. This first mechanical section 30 is equipped with second mechanical section 31 for synchronously moving the incidence position and photodetection position of the modulated light. Then this second mechanical section 31 outputs position signals indicating scanning positions and the position signals are supplied to the display/recording section 18 to be utilized for display or recording of the spatial distribution. Wavelength selector 11 is disposed in the post-stage of light source 10 for emitting the modulated light, so that modulated light of a desired wavelength can be selected with necessity. The other portions are the same as in the apparatus of the first embodiment described above.

The above arrangement used the modulated light of one wavelength, but modulated light of two or more wavelengths may be used in practice. Further, it is also possible to make the light incident to one light incidence position and to detect the propagating light. at two or more photodetection positions simultaneously or in time division.

Embodiment 3

Figure 8:
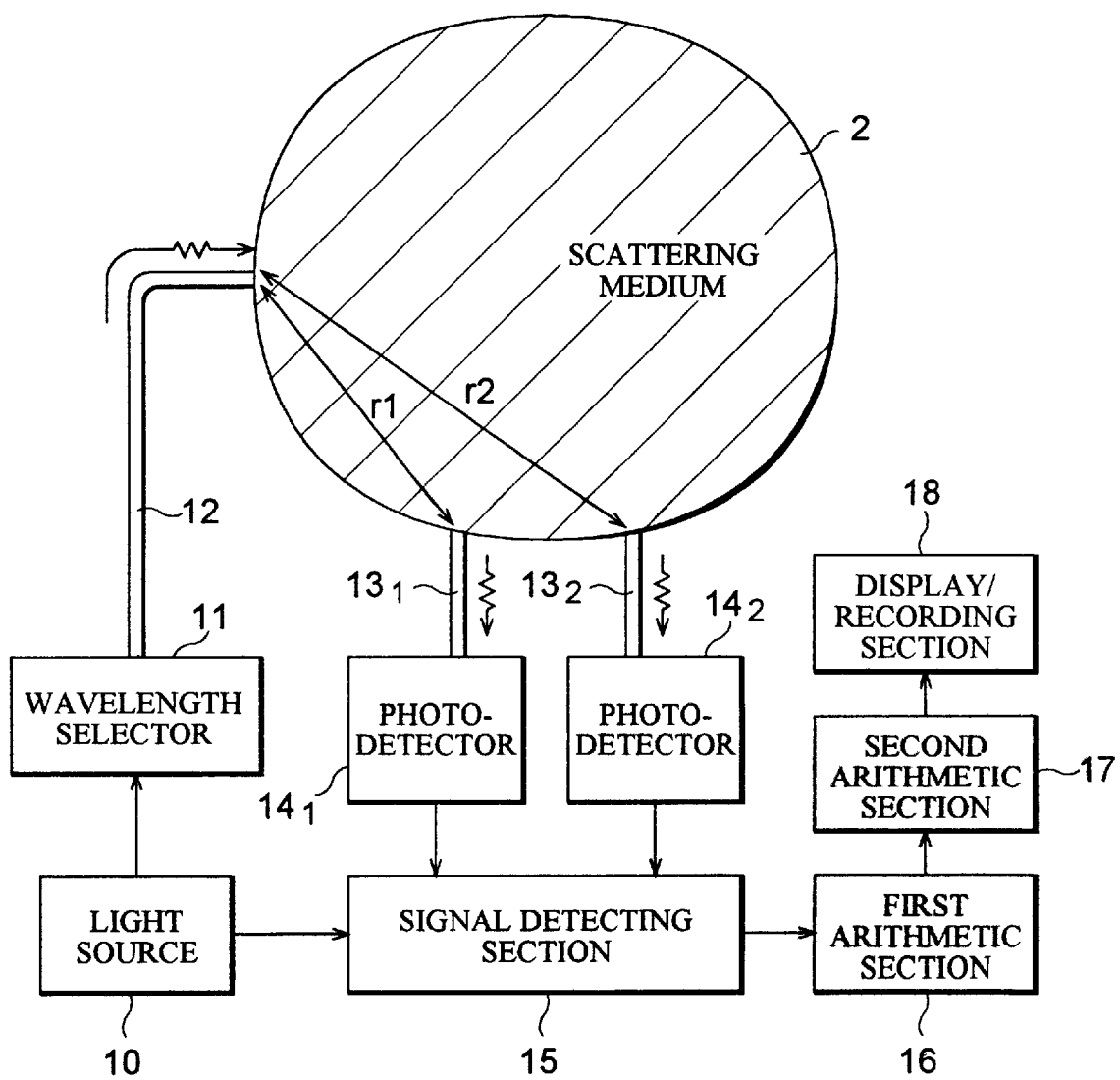
FIG. 8 is a schematic diagram of the configuration of the apparatus in the third embodiment according to the present invention.

FIG. 8 shows the third embodiment of the apparatus of the present invention for carrying out the method of the present invention and illustrates the configuration of the apparatus for measuring the concentration of absorptive constituent inside the scattering medium 2. In FIG. 8 the components having the same functions as those in FIG. 2 associated with the first embodiment and in FIG. 7 associated with the second embodiment are denoted by the same symbols. This configuration is arranged to use the modulated light of two wavelengths $\lambda_1$ and $\lambda_2$ and two photodetection distances $r_1$ and $r_2$. In this case, Eq. (15) described previously holds for each of measurements at the two photodetection distances $r_1$ and $r_2$. Accordingly, the difference between the absorption coefficients of the measured scattering medium 2 for the light of two wavelengths, $\mu_{a2}-\mu_{a1}$, can be obtained by eliminating the coefficient $b_2/b_1$ in Eq. (15) from simultaneous equations comprised of two equations based on Eq. (15). In this example, since the modulated light of two different wavelengths, at which the scattering coefficients are equal to each other or are regarded as equal to each other, is made incident to the scattering medium, k in aforementioned Eq. (15) can be k=1 and lnk is eliminated therefrom. For media of simple shape, $k=\mu'_{s1}/\mu'_{s2}$ may be assumed as described previously. From the above, the difference $\mu_{a2}-\mu_{a1}$ between the absorption coefficients of the medium containing a specific absorptive constituent for the light of the two wavelengths is calculated from Eq. (15) and the concentration of the absorptive constituent in the scattering medium can be quantified based on the relation shown in Eq. (13).

The light source 10 is a laser diode or the like and generates the modulated light of the two different wavelengths $\lambda_1$ and $\lambda_2$ and, for example, the modulation frequency f=100 MHz. The modulated light from the light source 10 is subjected to wavelength selection by the wavelength selector 11 and is guided through the light guide 12 to the surface of scattering medium 2 being the measured object. In this case, the apparatus may employ a method for making the modulated light beams of two wavelengths incident simultaneously and in this arrangement the wavelength selector 11 is omitted.

The space between the light guide 12 and the scattering medium 2 is very small in the embodiment of FIG. 8. In practice, however, this space may be widened and it may be filled with a liquid substance or a jelly substance (which will be called an interface material) having the refractive index and scattering coefficient nearly equal to those of the scattering medium 2, as in the first embodiment. Namely, the modulated light propagates in this interface material to enter the measured object without posing any problem. If reflection on the surface of scattering medium is problematic, influence of the surface reflection or the like can be decreased by properly selecting the interface material.

The light having propagated inside the scattering medium 2 is received by first and second light guides 13₁, 13₂ placed at the positions (photodetection positions) the distances $r_1$ and $r_2$ apart from the light incidence position. The interface material may also be used herein for the same reason as above.

The first photodetector 14₁ and second photodetector 14₂ convert respective light signals of the light received into electric signals, amplify them if necessary, and output measurement signals as to the measurements at the two photodetection distances $r_1$ and $r_2$. The photodetectors 14₁, 14₂ may be selected from the phototubes, photodiodes, avalanche photodiodes, PIN photodiodes, and so on, in addition to the photomultiplier tubes. In selection of the photodetectors, they need to have the spectral sensitivity characteristics for detecting the light of predetermined wavelengths and necessary time response speed. For weak light signals, high-gain photodetectors are used. Further, the time correlation photon counting method for counting photons may be applied. The places other than the light receiving surfaces of the photodetectors are desirably constructed in the structure for absorbing or intercepting the light. In the case wherein the modulated light of the two wavelengths is made incident simultaneously to the scattering medium as described above, wavelength selecting filters (not illustrated) are set at suitable positions between the photodetectors 14₁, 14₂ and the scattering medium 2.

The signal detecting section 15 and first arithmetic section 16 execute the following arithmetic based on the foregoing measurement signals respectively obtained in the measurements at the two photodetection distances $r_1$ and $r_2$. First, the signal detecting section 15 detects signals of the respective predetermined modulation frequency components from the measurement signals respectively obtained for the modulated light of the two wavelengths. In this case, the signal detecting section 15 utilizes a signal synchronized with the modulated light emitted from the light source 10 as occasion may demand. Next, the first arithmetic section 16 calculates the amplitudes A and inclinations (derivatives) $\partial\phi/\partial\omega$ of phase against modulation angular frequency from the respective signals of the predetermined modulation frequency components obtained for the modulated light of the two wavelengths.

The second arithmetic section 17 substitutes the above respective amplitudes A obtained at the two photodetection distances for the modulated light of the two wavelengths, and the inclinations of phase $\partial\phi/\partial\omega|_{\mu_x}$ obtained from the above respective inclinations of phase into aforementioned Eq. (15), solves simultaneous equations comprised of two equations obtained for the measurements at the two photodetection distances r, and $r_2$, calculates the difference $\mu_{a2}-\mu_{a1}$ (primary information) between the absorptive coefficients of the scattering medium 2 for the light having the two wavelengths, and further calculates the concentration of the absorptive constituent by use of aforementioned Eq. (13). For calculating the inclination of phase $\partial\phi/\partial\omega|_{\mu_{x3}}$, aforementioned Eq. (8) is applied and sufficient accuracy is secured with p=½. Since f=100 MHz, approximation $\partial\phi/\partial\omega\approx\phi/\omega$ may be applied as described above. In the case of f>100 MHz, measurements are conducted with the modulated light of the two modulation angular frequencies $\omega=\omega_1\pm\Delta\omega/2$ (>0) and $\partial\phi/\partial\omega|_{\mu_{x3}}$ is calculated using aforementioned Eq. (10). These arithmetic processes are carried out at high speed by microcomputers incorporated in the first and second arithmetic sections.

The above second arithmetic section 17 has a function to store the concentration information of absorptive constituent thus obtained and the display/recording means 18 is a section for displaying or recording these.

In the case wherein incident light intensities of the modulated light of the two wavelengths $\lambda_1$ and $\lambda_2$ to the scattering medium 2 are equal to each other or can be controlled so as to be equal, the second photodetector 14₂ can be omitted. In this case, the coefficient $b_2/b_1$ in aforementioned Eq. (15) becomes $b_2/b_1=1$ and $\ln(b_2/b_1)$ is eliminated therefrom. Thus, the difference $\mu_{a2}-\mu_{a1}$ (primary information) between the absorption coefficients of scattering medium 2 for the light of the two wavelengths can be calculated directly from Eq. (15) and the concentration of absorptive constituent can be further calculated using aforementioned Eq. (13).

The above described the method for making the light incident to one position and detecting the light at the two other positions. In practice, however, light beams of different wavelengths may be made incident at two positions and the light may be detected at another position in parallel or in time division.

The above third embodiment may employ either the method for making the light including beams of different wavelengths incident or the method for making the beams of different wavelengths incident in time division and using each beam. In the former case, either one method is selected from a method for forming coaxial beams of the light of the different wavelengths and selecting the wavelength by a wavelength selecting filter provided immediately before the light incidence position, a method for making the beams incident to the scattering medium as they are and selecting the wavelength by a wavelength selecting filter provided immediately before the photodetector, a method for splitting each detected light into two beams, subjecting them to wavelength selection, and detecting them in parallel by totally four photodetectors. In the latter case, either one device may be used from a light beam switching device using a mirror on the light source side, a wavelength switching device using a filter, a light switching device using an optical switch, and so on. The means for making the light incident to the scattering medium and the means for detecting the light having diffuse-propagated inside the scattering medium may be selected from those listed in the first embodiment.

The above first arithmetic section 16 was described as to the case for calculating the amplitude A and inclination $\partial\phi/\partial\omega$ of phase $\phi$ against modulation angular frequency from the signal of the predetermined modulation frequency component. However, it may calculate from the signal of the predetermined modulation frequency component either one combination of (i) the sine component with the inclination (derivative) of cosine component against modulation angular frequency, (ii) the cosine component with the inclination (derivative) of sine component against modulation angular frequency, or (iii) the phase with the inclination (derivative) of natural logarithm of amplitude against modulation angular frequency, as described previously. In that case, "amplitude A, inclination $\partial\phi/\partial\omega$ of phase $\phi$ against modulation angular frequency, and Eq. (15)" in above Embodiment 3 should read (i) "sine component, inclination (derivative) of cosine component against modulation angular frequency, and a similar equation to Eq. (15), derived from Eq. (5.1)," (ii) "cosine component, inclination (derivative) of sine component against modulation angular frequency, and a similar equation to Eq. (15), derived from Eq. (5.2)," or (iii) "phase, inclination (derivative) of natural logarithm of amplitude against modulation angular frequency, and a similar equation to Eq. (15), derived from Eq. (5.4)." Specifically, where $b_1=b_2$ and $\mu_{s1}=\mu_{s2}$, the above similar equations to Eq. (15) are Eq. (7.1) in the case of (i), Eq. (7.2) in the case of (ii), and Eq. (7.4) in the case of (iii). Accordingly, the third embodiment described herein can quantify the concentration of absorptive constituent by the four methods.

In the above third embodiment, when beams of three wavelengths are used, it becomes possible to measure concentrations of respective absorptive constituents in a scattering medium containing two types of absorptive constituents or to measure a concentration of one absorptive constituent and a total concentration of the other absorptive constituents in a scattering medium containing multiple types of absorptive constituents. For example, oxygenated hemoglobin and deoxygenated hemoglobin has different absorption coefficients depending upon the wavelengths, as shown in foregoing FIG. 3. Therefore, concentrations of these, and in addition, oxygen saturation or the like, can be measured by use of light of three wavelengths properly selected. In general, when light of n (where n is an integer of 2 or more) wavelengths is used, concentrations of (n−1) types of absorptive constituents can be measured. Further, the accuracy of concentration measurement of (n−1) types of absorptive constituents can be improved by using light of (n+1) or more types of wavelengths.

When the above measurement is carried out at different times (timings), a temporal change of concentration of a specific absorptive constituent can be measured. Further, a spatial distribution of concentration can be measured by synchronously moving the incidence position of light to the scattering medium and the photodetection position and measuring the concentration of absorptive constituent in each portion of the scattering medium. The above second arithmetic section 17 may be arranged to have a function to store the concentration information of absorptive constituent obtained in this way.

Embodiment 4

Figure 9:
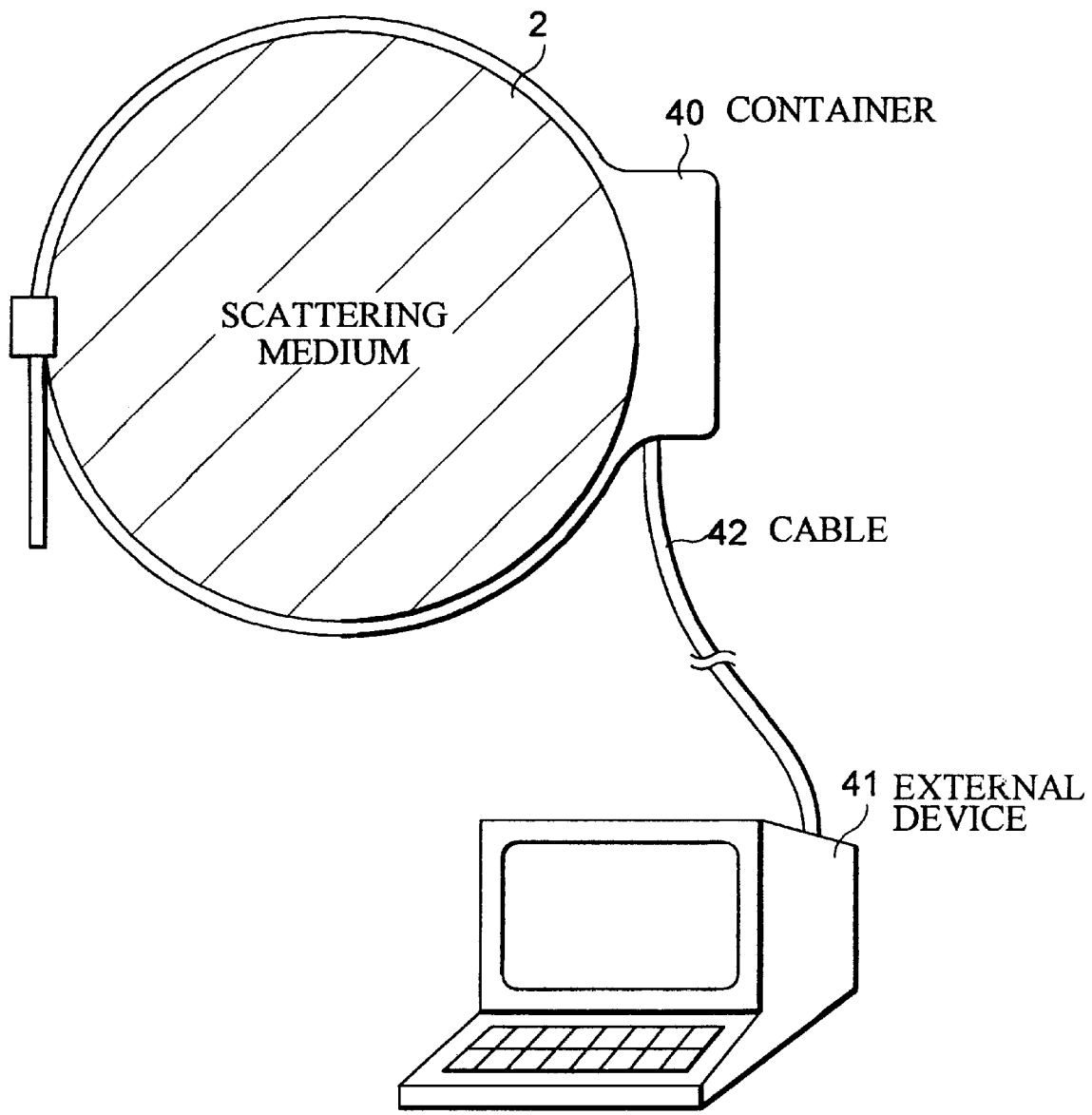
FIG. 9 is a schematic diagram of the configuration of the apparatus in the fourth embodiment according to the present invention.

FIG. 9 shows the fourth embodiment of the apparatus of the present invention for carrying out the method of the present invention and illustrates the configuration of the apparatus for measuring or monitoring a concentration of oxygenated hemoglobin inside the scattering medium 2 like the human head or an oxygen saturation of hemoglobin (a ratio of concentration of oxygenated hemoglobin to concentration of the whole hemoglobin). This fourth embodiment employs modulated light of three wavelengths $\lambda_1, \lambda_2, \lambda_3$ and two photodetection distances $r_1, r_2$. In this case, similarly as in the previous embodiments, three simultaneous equations of the four types are obtained based on either one of Eqs. (7.1) to (7.4) described previously. Accordingly, these simultaneous equations are solved, the difference (primary information) between absorption coefficients at each wavelength is calculated, and aforementioned Eq. (13) is further used to quantify the concentrations of oxygenated and deoxygenated hemoglobin and the oxygen saturation of hemoglobin or the like.

Figure 10:
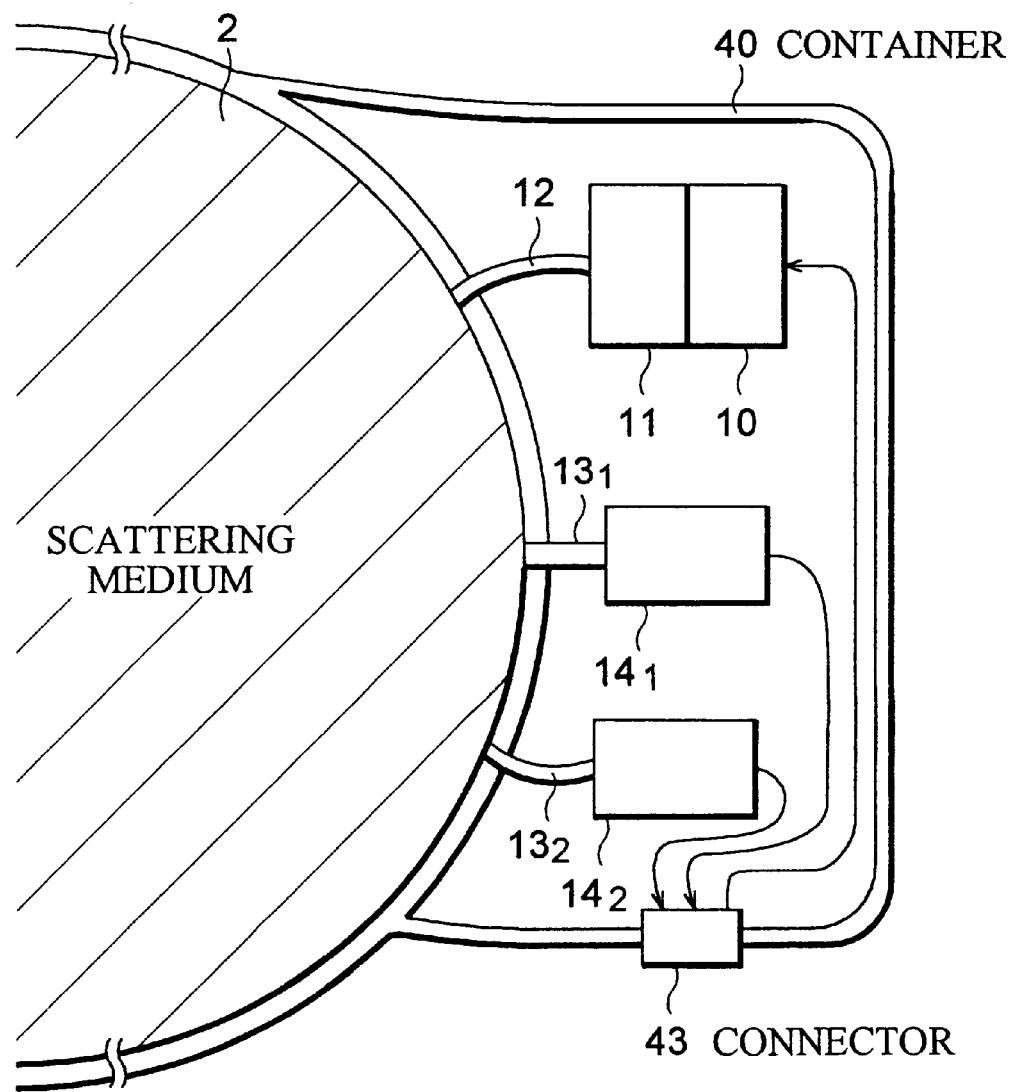
FIG. 10 is a schematic diagram of the configuration of the light incidence and detection section of the apparatus in the fourth embodiment.

The apparatus shown in FIG. 9 is provided with container 40 having a mounting band attached around the head 2 like a hair band, and external device 41 incorporating a signal detecting section, a first arithmetic section, a second arithmetic section, and a display/recording section is connected through cable 42 to the container 40. The apparatus shown in this embodiment uses the light of three predetermined wavelengths $\lambda_1, \lambda_2, \lambda_3$ and the operation thereof and each component device are almost the same as in the apparatus of the third embodiment. FIG. 10 illustrates the details of one portion of the apparatus shown in foregoing FIG. 9, i.e., the details of the inside of container 40.

As shown in FIG. 10, the light source 10, wavelength selector 11, first photodetector $14_1$, second photodetector $14_2$, and light guides 12, $13_1$, $13_2$ are built in the container 40 and the modulated light of the predetermined wavelengths $\lambda_1, \lambda_2, \lambda_3$ emitted from the light source 10 is subjected to wavelength selection by the wavelength selector 11 to be incident through the light guide 12 to the head 2. On this occasion, the three wavelengths are properly selected referring to the absorption spectra of hemoglobin shown in aforementioned FIG. 3.

The light having diffuse-propagated inside the head 2 is received by the light guides $13_1$, $13_2$ placed at the positions (photodetection positions) the distances $r_1$ and $r_2$ apart from the aforementioned light incidence position, is converted into electric signals by the first photodetector $14_1$ and second photodetector $14_2$, and is amplified if necessary. The power (power supply) and various signals are transmitted through connector 43 and signal cable 42 attached to the container 40 from the external device 41 and to the external device 41. The signal detecting section, first arithmetic section, second arithmetic section, and display/recording section (none of which is illustrated) placed in the external device 41 perform the same signal detection and arithmetics for the three wavelengths and the two photodetection distances as in the above third embodiment.

In the present embodiment, two simultaneous equations of the four types, similar to aforementioned Eq. (15), hold for signals obtained at the wavelengths $\lambda_1$ and $\lambda_2$ and at the wavelengths $\lambda_1$ and $\lambda_3$, signals obtained at the wavelengths $\lambda_1$ and $\lambda_2$ and at the wavelengths $\lambda_2$ and $\lambda_3$, or signals obtained at the wavelengths $\lambda_1$ and $\lambda_3$ and at the wavelengths $\lambda_2$ and $\lambda_3$. The above arithmetic processes are carried out at high speed by microcomputers or the like incorporated in the first and second arithmetic sections. Further, the signals in the container 40 can be converted into radio waves or light signals and they can be transmitted to the external device 41 without intervention of signal cable.

In the present embodiment described above, the light source, light incidence section, and photodetection means may be selected from those listed in the first embodiment. With the human head or the like, the surface reflection or the gap between the light guides and the head might pose a problem. In this case, the aforementioned interface material may be utilized well. In this case, removing the light guides shown in FIG. 10, the interface material having the scattering coefficient and absorption coefficient nearly equal to those of the measured object may be positioned between the head 2 and the wavelength selector 11 and between the head 2 and the photodetectors $14_1$ and $14_2$.

The apparatus as described can be used not only for the measurement of information in the brain, but also for measurement or monitoring of concentration of oxygenated hemoglobin in a leg muscle of a man in marathon, for example.

Embodiment 5

The fifth embodiment is arranged so that the modulated light of the three wavelengths $\lambda_1$, $\lambda_2$, $\lambda_3$ emitted from the light source in the above fourth embodiment is replaced by modulated light of a predetermined repetition frequency of an arbitrary waveform. Namely, the fourth embodiment used the sinusoidal modulated light of the predetermined angular frequency, but the modulated light may be of any waveform if it contains a specific frequency component, whereby the approach of the fourth embodiment can be applied as it is, to the specific frequency component contained in the light. For example, in the case of repetitive pulsed light, there are frequency components of the same frequency as the repetition frequency and integral multiples thereof and, therefore, the approach of the fourth embodiment can be applied to either one frequency component as it is. The performance that the modulated light of the predetermined repetition frequency is required to have is the stable repetition frequency and stable light intensity.

As described above, the absorption information measuring methods and apparatus of scattering medium according to the present invention enable to efficiently measure the concentration change or the absolute concentration of absorptive constituent inside the scattering medium of an arbitrary shape comprised of non-reentrant surfaces. Further, the present invention enables to measure the spatial distribution of the concentration change and the temporal change and spatial distribution of concentration. Further, since the methods and apparatus of the present invention utilize the modulated light, the utilization factor of light is high and signal-to-noise ratios are large, thus achieving the high measurement accuracy. Therefore, the methods and apparatus of the present invention allow accurate and efficient real-time measurements of oxygen amounts in the brain, oxygen amounts in a leg muscle of a man under motion, concentrations of absorptive constituents in a living tree, and so on.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

The basic Japanese Application No. 230683/1996(8-230683) filed on Aug. 30, 1996 is hereby incorporated by reference.

What is claimed is:

1. A method of measuring absorption information of a scattering medium, said method comprising:

applying modulated light having a predetermined modulation frequency component to form a spot shape incident on a surface of a scattering medium comprising a measured object;

acquiring respective measurement signals by receiving said modulated light having propagated inside said measured object at one or both of a plurality of different times and a plurality of positions on said surface of said scattering medium;

detecting, from each of said respective measurement signals, respective signals of said modulation frequency component;

obtaining, from said respective signals of said modulation frequency component, amplitude components and phase component slopes against modulation angular frequency; and calculating a difference between absorption coefficients of said measured object based upon a predetermined relation among said amplitude components, said phase component slopes against modulation angular frequency, and a difference between absorption coefficients corresponding to different ones of said respective measurement signals.

2. A method according to claim 1, wherein a difference of concentration of an absorptive constituent is quantified based upon a predetermined relation among said difference between absorption coefficients, an absorption coefficient per unit concentration of an absorptive constituent, and said difference of concentration of said absorptive constituent.

3. A method of measuring absorption information of a scattering medium, said method comprising:

applying a plurality of modulated light beams to form a spot shape incident on a surface of a scattering medium comprising a measured object, each of said plurality of modulated light beams having a predetermined modulation frequency component and a different wavelength at which scattering coefficients of said measured object are substantially equal to one another;

acquiring respective measurement signals for said different wavelengths by receiving said modulated light beams having propagated inside said measured object at a predetermined position on said surface of said scattering medium;

detecting, from each of said respective measurement signals, respective signals of said modulation frequency component;

obtaining, from said respective signals of said modulation frequency component, amplitude components and phase component slopes against modulation angular frequency; and calculating a difference between absorption coefficients of said measuring object at said respective wavelengths based upon a predetermined relation among said amplitude components, said phase component slopes against modulation angular frequency, and said difference between absorption coefficients of said measured object at said respective wavelengths.

4. The method according to claim 3, further comprising quantifying a concentration of the absorptive constituent based upon a predetermined relation among said difference between absorption coefficients, absorption coefficients per unit concentration of an absorptive constituent at said respective wavelengths, and said concentration of said absorptive constituent.

5. The method according to claim 3, wherein said measurement signals comprise a plurality of measurement signals obtained when said light beams are received at a plurality of different positions in said surface of said scattering medium.

6. An apparatus for measuring absorption information of a scattering medium, said apparatus comprising:

a light source, configured and arranged to apply modulated light having a predetermined modulation frequency component to form a spot shaped incident on a surface of a scattering medium comprising a measured object;

a photodetector, configured and arranged to acquire respective measurement signals by receiving said modulated light having propagated inside said measured object at one or both of a plurality of different times and a plurality of positions on said surface of said scattering medium;

a signal detector, configured and arranged to detect, from said respective measurement signals, respective signals of said modulation frequency component;

a first arithmetic section, configured and arranged to calculate, from said respective signals of said modulation frequency component, amplitude components and phase component slopes against modulation angular frequency; and a second arithmetic section for calculating a difference between absorption coefficients of said measuring object based upon a predetermined relation among said amplitude components, said phase component slopes against modulation angular frequency, and said difference between absorption coefficients of said measuring object.

7. The apparatus according to claim 6, wherein said second arithmetic section further is configured and arranged to calculate a difference of concentration of an absorptive constituent based upon a predetermined relation among said difference between absorption coefficients, an absorption coefficient per unit concentration of said absorptive constituent, and said difference of concentration of said absorptive constituent.

8. An apparatus for measuring absorption information of a scattering medium, said apparatus comprising:

a light source, configured and arranged to apply a plurality of modulated light beams to form a spot shaped incident on a surface of a scattering medium comprising a measured object, each of said plurality of modulated light beams having a predetermined modulation frequency component and having a predetermined different wavelength at which scattering coefficients of said measured object are substantially equal to one another;

a photodetector, configured and arranged to acquire respective measurement signals for said different wavelengths by receiving said modulated light beams having propagated inside said measured object at a predetermined position in said surface of said scattering medium;

a signal detector, configured and arranged to detect, from said respective measurement signals, respective signals of said modulation frequency component;

a first arithmetic section for obtaining, from said respective signals of said modulation frequency component, amplitude components and phase component slopes against modulation angular frequency; and a second arithmetic section for calculating a difference between absorption coefficients of said measuring object based upon a predetermined relation among said amplitude components, said phase component slopes against modulation angular frequency, and said difference between absorption coefficients.

9. The apparatus according to claim 8, wherein said second arithmetic section further quantifies a concentration of an absorptive constituent based upon a predetermined relation among said difference between absorption coefficients, absorption coefficients per unit concentration of an absorptive constituent at said different wavelengths, and said concentration of said absorptive constituent.

10. The apparatus according to claim 8, wherein said photodetector comprises a light receiver capable of receiving said light beams at a plurality of positions in said surface of said scattering medium, and wherein said measurement signals comprise a plurality of measurement signals obtained when said light beams are received at a plurality of positions in said surface of said scattering medium.

* * * * *